(12) United States Patent
Borchers

(10) Patent No.: US 7,846,748 B2
(45) Date of Patent: Dec. 7, 2010

(54) METHODS OF QUANTITATION AND IDENTIFICATION OF PEPTIDES AND PROTEINS

(75) Inventor: Christoph H. Borchers, Apex, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/411,704

(22) Filed: Apr. 11, 2003

(65) Prior Publication Data

US 2004/0214338 A1    Oct. 28, 2004

Related U.S. Application Data

(60) Provisional application No. 60/430,234, filed on Dec. 2, 2002.

(51) Int. Cl.
| | |
|---|---|
| G01N 33/53 | (2006.01) |
| G01N 33/536 | (2006.01) |
| G01N 33/537 | (2006.01) |
| G01N 33/543 | (2006.01) |
| C12N 11/00 | (2006.01) |
| G01N 1/00 | (2006.01) |

(52) U.S. Cl. .................. 436/523; 435/7.1; 435/174; 435/175; 435/176; 435/177; 435/973; 435/287.1; 435/287.2; 436/518; 436/528; 436/529; 436/530; 436/531; 436/532; 436/533; 436/535; 436/175; 436/177; 427/2.11; 427/2.13; 427/533; 427/554

(58) Field of Classification Search ......... 435/174–177, 435/283.1, 288.6, 7.1, 7.92, 973, 287.1, 287.2; 436/161, 173, 518–542, 175, 177, 178; 422/69, 422/70–71, 101; 530/413; 427/2.11, 2.13, 427/553, 554
See application file for complete search history.

(56) References Cited

U.S. PATENT DOCUMENTS

| | | | | |
|---|---|---|---|---|
| 5,670,381 | A | * | 9/1997 | Jou et al. ................. 436/518 |
| 5,719,060 | A | * | 2/1998 | Hutchens et al. .......... 436/174 |
| 5,894,063 | A | * | 4/1999 | Hutchens et al. .......... 436/155 |

(Continued)

FOREIGN PATENT DOCUMENTS

CA        2504413        10/2002

(Continued)

OTHER PUBLICATIONS

Hanke, T. et al. Immunogenicities of intravenous and intramuscular administrations of modified vaccinia virus Ankara-based multi-CTL epitope vaccine for human immunodeficiency virus type 1 in mice. J. Gen. Virol. 1998;79:83-90.*

(Continued)

*Primary Examiner*—Unsu Jung
(74) *Attorney, Agent, or Firm*—Jenkins, Wilson, Taylor & Hunt, PA

(57) ABSTRACT

The present invention provides methods of quantifying the amount or concentration of one or more peptides and/or proteins in one or more samples using differentially isotopically-labeled peptides and/or proteins. The invention also provides methods of identifying one or more peptides and/or proteins in one or more samples.

17 Claims, 13 Drawing Sheets

U.S. PATENT DOCUMENTS

| | | | |
|---|---|---|---|
| 6,020,208 A * | 2/2000 | Hutchens et al. | 436/174 |
| 6,027,942 A * | 2/2000 | Hutchens et al. | 436/173 |
| 6,225,047 B1 * | 5/2001 | Hutchens et al. | 435/5 |
| 6,379,970 B1 | 4/2002 | Liebler et al. | |
| 6,391,649 B1 * | 5/2002 | Chait et al. | 436/174 |
| 6,528,320 B2 | 3/2003 | Hutchens et al. | |
| 6,579,719 B1 | 6/2003 | Hutchens et al. | |
| 6,629,040 B1 * | 9/2003 | Goodlett et al. | 702/23 |
| 6,670,194 B1 * | 12/2003 | Aebersold et al. | 436/173 |
| 6,811,969 B1 | 11/2004 | Hutchens et al. | |
| 6,881,586 B2 | 4/2005 | Hutchens et al. | |
| 6,905,879 B2 * | 6/2005 | Qiu et al. | 436/86 |
| 6,906,338 B2 * | 6/2005 | Tajima | 250/505.1 |
| 2002/0055186 A1 | 5/2002 | Barry et al. | |
| 2002/0076817 A1 | 6/2002 | Figeys et al. | |
| 2002/0090652 A1 | 7/2002 | Fu et al. | |
| 2002/0182649 A1 | 12/2002 | Weinberger et al. | |
| 2002/0192720 A1 | 12/2002 | Parker et al. | |
| 2003/0044864 A1 | 3/2003 | Short et al. | |
| 2003/0219731 A1 * | 11/2003 | Weinberger et al. | 435/5 |
| 2004/0038307 A1 | 2/2004 | Lee et al. | |
| 2004/0180380 A1 | 9/2004 | Lee et al. | |
| 2005/0069911 A1 | 3/2005 | Lee et al. | |

FOREIGN PATENT DOCUMENTS

| | | |
|---|---|---|
| JP | A H08-329884 | 12/1996 |
| JP | A H09-061597 | 3/1997 |
| JP | A2003-501790 | 1/2003 |
| WO | WO 00/11208 A1 | 3/2000 |
| WO | WO00/73750 | 12/2000 |
| WO | 02/25287 A2 | 3/2002 |
| WO | WO 03/014302 A2 | 2/2003 |
| WO | WO03/044221 | 5/2003 |
| WO | WO2009/103984 | 8/2009 |

OTHER PUBLICATIONS

Legros, V. et al. Characterization of an anti-Borrelia burgdorferi OspA conformational epitope by limited proteolysis of monoclonal antibody-boudn antigen and mass spectrometric peptide mapping. Protein Sci. 2000;9:1002-1010.*

Palker et al., "Type-specific neutralization of the human immunodeficiency virus with antibodies to env-encded synthetic peptides" Prol. Natl. Acad. Sci. USA, 1988, vol. 85, pp. 1932-1936.*

Hochleitner, Elisabeth O., et al., "Characterization of a discontinuous epitope of the human immunodeficiency virus (HIV) core protein p24 by epitope excision and differential chemical modification followed by the mass spectrometric peptide mapping analysis", Protein Science, vol. 9: 487-496, 2000.

Hochleitner, Elisabeth O., et al., "Mass Spectrometric Characterization of a Discontinuous Epitope of the HIV Envelope Protein HIV-gp120 Recognized by the Human Monoclonal Antibody 1331A", The Journal of Immunology, vol. 164, No. 8: 4156-4161, 2000.

Parker, Carol E., et al., "Fine Definition of the Epitope of the gp41 Glycoprotein of Human Immunodeficiency Virus Type 1 for the Neutralizing Monoclonal Antibody 2F5", Journal of Virology, vol. 75, No. 22: 10906-10911, Nov. 2001.

Raska, C.S., et al., "Direct MALDI-MS/MS of Peptides Bound to Affinity Media", presented at the 50th Annual Conference on Mass Spectrometry and Allied Topics, Orlando, FL, Jun. 2-6, 2002.

Raska, Christina S., et al., "Direct MALDI-MS/MS of Phosphopeptides Affinity-Bound to Immobilized Metal Ion Affinity Chromatography Beads", Analytical Chemistry, vol. 74, No. 14: 3429-3433, Jul. 15, 2002.

Scrivener, Elaine, et al., "Peptidomics: A new approach to affinity protein microarrays", Proteomics, vol. 3, No. 2: 122-128, Feb. 2003.

Sunnarborg, Susan Wohler, et al., "Tumor Necrosis Factor-α Coverting Enzyme (TACE) Regulates Epidermal Growth Factor Receptor Ligand Availablity", The Journal of Biological Chemistry, vol. 277, No. 15: 12838-12845, Apr. 12, 2002.

Cretich et al., "Protein and peptide arrays: Recent trends and new directions," Biomolecular Engineering, vol. 23, pp. 77-88 (2006).

Jiang et al., "An immunoaffinity tandem mass spectrometry (iMALDI) assay for detection of Francisella tularensis," Analytica Chimica Acta, vol. 605, pp. 70-79 (2007).

Jiang et al., "Development of an immuno tandem mass spectrometry (iMAIDI) assay for EGFR diagnosis," Proteomics Clin. Appl., vol. 1, pp. 1651-1659 (2007).

Krishnamurthy, "Rapid Identification of Bacteria by Direct Matrix-assisted Laser Desorption/Ionization Mass Spectrometric Analysis of Whole Cells," Rapid Communications in Mass Spectrometry, vol. 10, 1992-1996 (1996).

Leenheer et al., "Applications of isotope dilution-mass spectrometry in clinical chemistry, pharmacokinetics, and toxicology," Mass Spectrometry Reviews, vol. 11, pp. 249-307 (1992).

Mann et al., "Error-Tolerant Identification of Peptides in Sequence Databases by Peptide Sequence Tags," Anal. Chern., vol. 66, pp. 4390-4399 (1994).

Mortz et al., "Sequence tag identification of intact proteins by matching tandem mass spectral data against sequence data bases," Proc. Natl. Acad. Sci. USA, vol. 93, pp. 8264-8267 (Aug. 1996).

Oda et al., "Accurate quantitation of protein expression and site-specific phosphorylation," Proc. Natl. Acad. Sci. USA, vol. 96, pp. 6591-6596 (Jun. 1999).

Sadygov et al., "Large-scale database searching using tandem mass spectra: Looking up the answer in the back of the book," Nature Methods, vol. 1, No. 3, pp. 195-202 (Dec. 2004).

Shevchenko et al., "Linking genome and proteome by mass spectrometry: Large-scale identification of yeast proteins from two dimensional gels," Proc. Natl. Acad. Sci. USA, vol. 93, pp. 14440-14445 (Dec. 1996).

Solassol et al., "Clinical proteomics and mass spectrometry profiling for cancer detection," Expert Rev. Proteomics, vol. 3, No. 3, pp. 311-320 (2006).

Zhou et al., "Quantitative proteome analysis by solid-phase isotope tagging and mass spectrometry," Nature Biotechnology, vol. 19, p. 512-515 (May 2002).

Gevaert et al., A peptide concentration and purification method for protein characterization in the subpicomole range using matrix assisted laser desorption/ionization-postsource decay (MALDI-PSD) sequencing. Electrophoresis. vol. 19 pp. 909-917 (1998).

Gevaert et al., Peptides adsorbed on reverse-phase chromatographic beads as targets for femtomole sequencing by post-source decay matrix assisted laser desorption ionization-reflectron time of flight mass spectrometry (MALDI-RETOF-MS). Electrophoresis. vol. 18 pp. 2950-2960 (1997).

Hurst et al., "Analysis for TNF-α using Solid-Phase Affinity Capture with Radiolabel and MALDI-MS Detection," Anal. Chem., vol. 71, pp. 4727-4733 (1999).

Office Communication corresponding to Canadian Patent Application No. 2,507,864 dated Jul. 2, 2009.

Biemann K., "Contributions of mass spectrometry to peptide and protein structure," Biomed. Environ. Mass Spectrom, vol. 16, No. 1-12, pp. 99-111 (1988).

Doucette et al., "Protein concentration and enzyme digestion on microbeads for MALDI-TOF peptides mass mapping of proteins from dilute solutions," Anal. Chem., vol. 72, pp. 3355-3362 (Jul. 15, 2000).

Genbank Accession No. NP_000199.

Office Communication corresponding to Canadian Patent Application No. 2,507,864 dated Apr. 29, 2010.

Office Communication corresponding to Japanese Patent Application No. 2006/515045 dated Feb. 26, 2010.

Roepstorff P, Fohlman J: Proposal for a common nomenclature for sequence ions in mass spectra of peptides. Biomed Mass Spectrom 1984, 11(11):601.

S. P. Gygi et al., "Quantitative analysis of complex protein mixtures using isotope-coded affinity tags", Nat. Biotechnol., vol. 17, Oct. 1999, pp. 994-999.

* cited by examiner

US 7,846,748 B2

METHODS OF QUANTITATION AND IDENTIFICATION OF PEPTIDES AND PROTEINS

RELATED APPLICATIONS

This application claims the priority benefit of U.S. Provisional Application No. 60/430,234, filed on Dec. 2, 2002, the entire content of which is hereby incorporated by reference.

FIELD OF THE INVENTION

The present invention generally relates to methods of quantifying the amount or concentration of one or more peptides and/or proteins in one or more samples as well as to methods of identifying one or more peptides and/or proteins in one or more samples.

BACKGROUND OF THE INVENTION

Recent biomedical research has focused on proteomics, with an emphasis on the diagnosis and treatment of diseases by determining the expression profiles of disease-related proteins. Methods and technologies of identifying and quantifying proteins and comparing expression levels of proteins have thus become important. Various technologies have been developed to accommodate such proteomic research, many of which include the use of mass spectrometry.

For example, U.S. Pat. No. 6,379,970 relates to a method of detecting peptide fragments of proteins that are differentially present in biological samples. The patent states that the identity of the peptides may be determined and correlated with the proteins that are differentially present in the samples.

U.S. Patent Application Publication No. U.S. 2002/0076817 relates to methods useful in the labeling of multiple polypeptide samples and subsequent analysis of the samples by mass spectrometry, particularly in the high throughput proteomic setting.

U.S. Patent Application Publication No. 2002/0192720 relates to methods using gel electrophoresis and mass spectrometry for the rapid, quantitative analysis of proteins or protein function in mixtures of proteins derived from two or more samples in one unit operation.

U.S. Patent Application Publication No. 2003/0044864 relates to proteomics and mass spectrometry technology. The publication states that the invention provides methods for determining polypeptide profiles and protein expression variations and methods of simultaneously identifying and quantifying individual proteins in complex protein mixtures by selective differential labeling of amino acid residues followed by chromatographic and mass spectrographic analysis.

Although many new technologies have been developed, it would be advantageous to provide improved methods for quantitative analysis of peptides and proteins that do not require separation techniques such as chromatography or electrophoresis.

SUMMARY OF THE INVENTION

The present invention generally relates to methods of quantifying the amount or concentration of one or more peptides and/or proteins in one or more samples as well as to methods of identifying one or more peptides and/or proteins in one or more samples. In one aspect of the invention, a method of quantifying the amount or concentration of a peptide in two different samples is provided. A first sample containing an amount of a peptide and a second sample containing an amount of the peptide are provided. The peptide in the first sample and the peptide in the second sample are differentially isotopically-labeled such that the peptide in the first sample has a different molecular weight than the peptide in the second sample. A substrate having a plurality of isolation agents immobilized thereon is also provided, with each of the isolation agents having an affinity for the peptide. The differentially isotopically-labeled peptides are isolated using the isolation agents immobilized on the substrate. The differentially isotopically-labeled peptides are then analyzed using matrix-assisted laser desorption/ionization mass spectrometry (MALDI-MS) to determine the relative amounts or concentrations of the peptide in the first sample and the second sample. The substrate having the isolation agents immobilized thereon is placed on a MALDI target either before, during, or after the peptide is isolated using the isolation agents.

In another aspect of the invention, a method of quantifying the amount or concentration of a peptide in two different samples is provided. A first sample containing an amount of a peptide that has a continuous epitope and a second sample containing an amount of the peptide are provided. The peptide in the first sample and the peptide in the second sample are differentially isotopically-labeled such that the peptide in the first sample has a different molecular weight than the peptide in the second sample. A substrate having a plurality of antibodies immobilized thereon is also provided, with each of the antibodies having a paratope specific to the continuous epitope of the peptide. The differentially isotopically-labeled peptides are isolated using the antibodies immobilized on the substrate. The differentially isotopically-labeled peptides are then analyzed using MALDI-MS to determine the relative amounts or concentrations of the peptide in the first sample and the second sample. The substrate having the antibodies immobilized thereon is placed on a MALDI target either before, during, or after the peptide is isolated using the antibodies.

In yet another aspect of the invention, a method of quantifying the amount or concentration of a protein in two different samples is provided. A first sample containing an amount of a protein that has a discontinuous epitope and a second sample containing an amount of the protein are provided. The protein in the first sample and the protein in the second sample are differentially isotopically-labeled such that the protein in the first sample has a different molecular weight than the protein in the second sample. A substrate having a plurality of antibodies immobilized thereon is also provided, with each of the antibodies having a paratope specific to the discontinuous epitope of the protein. The differentially isotopically-labeled proteins are isolated using the antibodies immobilized on the substrate and the differentially isotopically-labeled proteins are digested to produce differentially isotopically-labeled peptides that remain isolated by the antibodies. The differentially isotopically-labeled peptides are then analyzed using MALDI-MS to determine the relative abundances of the differentially isotopically-labeled peptides. The relative amounts or concentrations of the protein in the first sample and the second sample are then determined based on the relative abundances of the differentially isotopically-labeled peptides.

In a further aspect of the invention, a method of determining the identity of an epitope-containing peptide is provided. A sample is provided that contains an amount of a peptide having an epitope. A substrate having a plurality of antibodies immobilized thereon is also provided, with each of the antibodies immobilized thereon having a paratope specific to the epitope of the peptide. The peptide is isolated using the antibodies immobilized on the substrate. The amino acid sequence of the peptide is then determined by analyzing the peptide using matrix-assisted laser desorption/ionization tandem mass spectrometry (MALDI-MS/MS) and performing one or both of database searching and de novo sequencing using the results of the MALDI-MS/MS analysis. The substrate having the antibodies immobilized thereon is placed on a MALDI target either before, during, or after the peptide is isolated using the antibodies. In some embodiments, the substrate has a volume of $150^3$ μm$^3$ or less and/or has no other antibodies immobilized thereon.

In yet a further aspect of the invention, a method of identifying a protein of interest in a sample is provided. A protein-containing sample is provided that contains a protein of interest having a continuous epitope. A substrate having a plurality of antibodies immobilized thereon is also provided, with each of the antibodies immobilized thereon having a paratope specific to the continuous epitope of the protein. The protein is digested to produce a peptide having the continuous epitope of the protein. The peptide having the continuous epitope is isolated using the antibodies immobilized on the substrate. The peptide is analyzed using MALDI-MS/MS. The peptide is then correlated with the identity of a corresponding protein by performing database searching using the results of the MALDI-MS/MS analysis. The substrate having the antibodies immobilized thereon is placed on a MALDI target either before, during, or after the peptide is isolated using the antibodies. In some embodiments, the substrate has a volume of $150^3$ μm$^3$ or less and/or has no other antibodies immobilized thereon.

In another aspect of the invention, a method of identifying a protein of interest in a sample is provided. A protein-containing sample is provided that contains a protein of interest having a discontinuous epitope. A substrate having a plurality of antibodies immobilized thereon is also provided, with each of the antibodies having a paratope specific to the discontinuous epitope of the protein. The protein having the discontinuous epitope is then isolated using the antibodies immobilized on the substrate. The protein is digested to produce one or more peptides that remain isolated by the antibodies. The peptide or peptides that remain isolated by the antibodies are analyzed using MALDI-MS/MS. The peptide or peptides are then correlated with the identity of a corresponding protein by performing database searching using the results of the MALDI-MS/MS analysis. The substrate having the antibodies immobilized thereon is placed on a MALDI target either before, during, or after the protein is isolated using the antibodies.

DETAILED DESCRIPTION OF THE INVENTION

Figure 1:
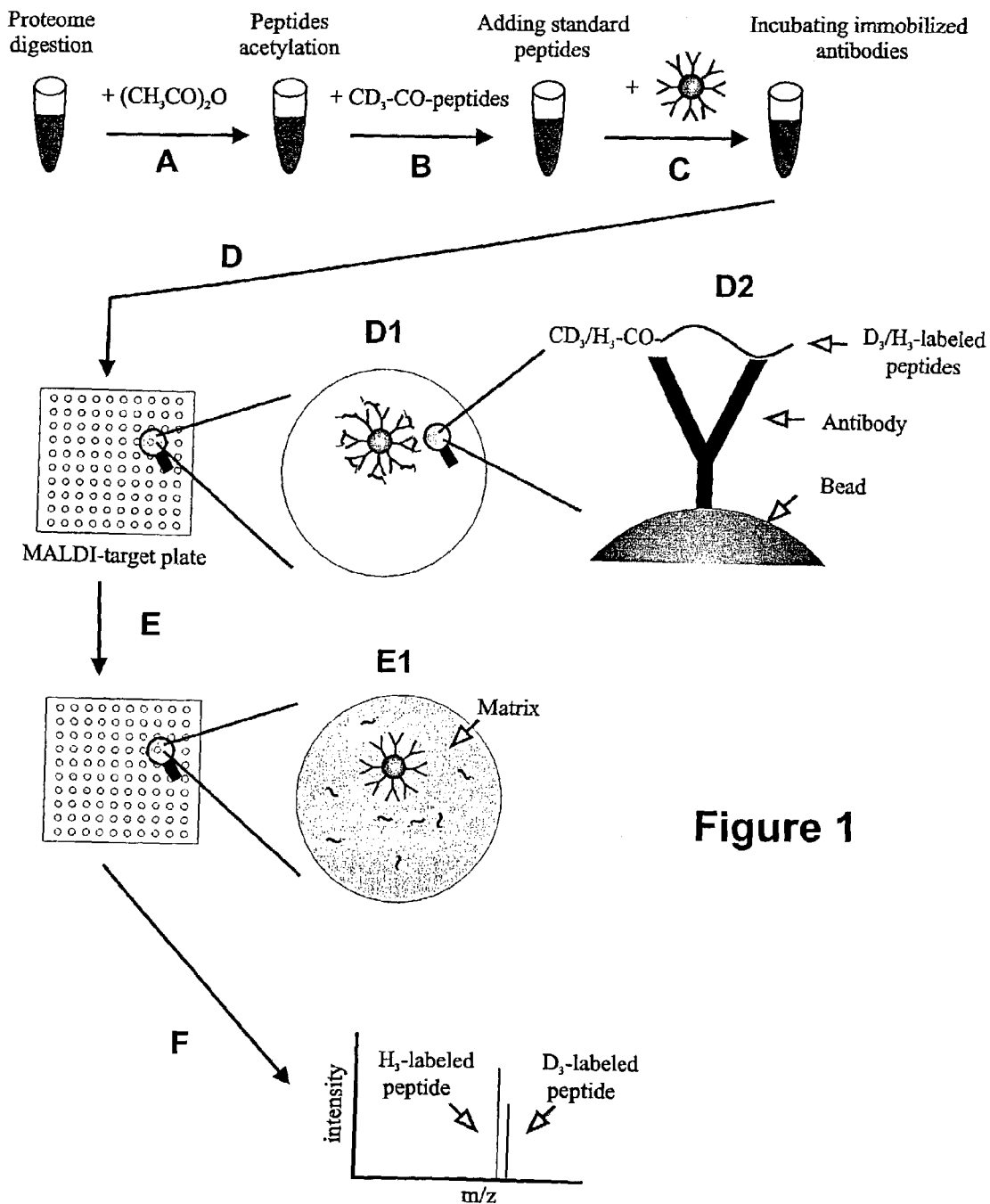
FIG. 1 illustrates an analytical scheme of one embodiment of a method for quantitative peptide/protein expression analysis using MALDI-MS.

The present invention relates to methods of quantifying the amounts and/or concentrations of one or more peptides and/or proteins in one or more samples using mass spectrometry as well as to methods of identifying one or more peptides and/or proteins in one or more samples using mass spectrometry. Prior to describing this invention in further detail, however, the following terms will first be defined.

DEFINITIONS

"MALDI-MS" means matrix-assisted laser desorption/ionization mass spectrometry, and includes any type of mass spectrometry using MALDI, including, but not limited to MALDI time-of-flight mass spectrometry (MALDI-TOF-MS), MALDI quadrupole/time-of-flight mass spectrometry (MALDI-QqTOF-MS), MALDI Fourier transform ion cyclotron resonance mass spectrometry (MALDI-FTICR), and MALDI-quadrupole ion trap mass spectrometry. As used herein, "MALDI" or "matrix-assisted laser desorption/ionization mass spectrometry" includes atmospheric pressure matrix-assisted laser desorption/ionization mass spectrometry (AP-MALDI).

"MALDI-MS/MS" means matrix-assisted laser desorption/ionization tandem mass spectrometry and includes any type of tandem mass spectrometry using MALDI, including, but not limited to, MALDI quadrupole/time-of-flight tandem mass spectrometry (MALDI-QqTOF-MS/MS), MALDI time-of-flight/time-of-flight tandem mass spectrometry (MALDI-TOF/TOF), and MALDI Fourier transform ion cyclotron resonance tandem mass spectrometry (MALDI-FTICR-MS/MS).

"Peptide" means a compound of two or more amino acids and includes modified and unmodified peptides.

"Amino acid" includes naturally-occurring and synthetic amino acids and includes modified and unmodified amino acids.

"Modified" means, with respect to peptides and amino acids, any modification to a peptide or amino acid structure, including posttranslational modifications. Peptide and amino acid modifications are known to those skilled in the art. Modifications to peptides and amino acids include, but are not limited to phosphorylation, acetylation, O-glycosylation, N-glycosylation, acylation, oxidation, hydroxylation, myristoylation, farnesylation, methylation, glutathionylation, palmitoylation, cysteinylation, stearoylation, formylation, deamidation, and carboxylation.

"Isolation agent" means any agent that may be immobilized on a substrate and that has an affinity for, a binding specificity for, or an ability to interact with a peptide such that the peptide may be isolated by the isolation agent. Isolation agents include, but are not limited to antibodies, avidin, biotin, receptors, proteins, and peptides.

"Antibody" means any immunoglobulin, including antibodies and fragments thereof, that binds a specific epitope.

"Differentially isotopically-labeled" means, with respect to two or more peptides or proteins, that each of the two or more peptides or proteins is chemically identical (i.e., has the same amino acid sequence and modifications) other than differential isotopes present in the two or more peptides or proteins that cause the molecular weights of the otherwise identical peptides or proteins to be different. Various methods may be used to differentially isotopically-label two or more peptides or proteins. When peptides originate from proteins, the differentially isotopically-labeled peptides may be produced by labeling the proteins before digestion such that labeled peptides are formed upon digestion of the proteins, labeling the peptides during protein digestion, or labeling the peptides after protein digestion.

Quantitation of Amount/Concentration of Peptides/Proteins

The present invention provides methods of quantifying the amount and/or concentration of one or more peptides and/or proteins in one or more samples. The invention includes methods for relatively quantifying the amount and/or concentration of one or more peptides or proteins of interest in two or more different samples containing the peptides or proteins of interest and methods for absolutely quantifying the amount and/or concentration of one or more peptides or proteins of interest in one or more samples.

According to one aspect of the invention, at least two samples (e.g., first and second samples) are provided that each contain an amount of the same peptide (or are believed to contain an amount of the peptide). The peptide in each sample is differentially isotopically-labeled such that the peptide in each sample has a different molecular weight than the peptide in the other samples but has the same amino acid sequence. For example, when two samples are used, the peptide from the first sample and the peptide from the second sample are differentially isotopically-labeled such that the peptide from the first sample has a different molecular weight than the peptide from the second sample but has the same amino acid sequence as the peptide from the second sample. As discussed below, the samples containing the peptide (or believed to contain the peptide) may originate from any source and the peptide or peptides may be differentially isotopically-labeled by various methods.

The differentially isotopically-labeled peptides are isolated using a substrate having a plurality of isolation agents (e.g., antibodies) immobilized thereon. Each of the isolation agents has a specific affinity or binding specificity for the peptide. It is preferred that each substrate have only one type of isolation agent immobilized thereon (i.e., it is preferred that all of the isolation agents on a substrate have the same affinity or specificity for the same peptide). In some embodiments, however, isolation agents with an affinity or specificity for different peptides may be present on the same substrate. When the isolation agents are antibodies, each of the antibodies has a paratope specific to an epitope of the peptide. Although the antibodies preferably have a paratope specific to a continuous epitope of the peptide, antibodies having a paratope specific to a discontinuous epitope of a protein and/or peptide may be used as further explained below.

Either before, during, or after isolating the differentially isotopically-labeled peptides on the substrate, the substrate is positioned on a MALDI target (e.g., on a spot of a metal MALDI target plate) such that the differentially isotopically-labeled peptides may be analyzed by MALDI-MS and/or MALDI-MS/MS. Any MALDI target could be used, including, but not limited to, stainless steel MALDI targets, silver-coated MALDI targets, and Anchor Chip MALDI targets (Bruker).

The differentially isotopically-labeled peptides are then analyzed by MALDI-MS to determine the relative amounts of the peptide in the first sample and the second sample. Any suitable MALDI matrix may be used for the MALDI-MS including, but not limited to alpha-cyano-4-hydroxycinnamic acid (HCCA) and 2,5-dihydrobenzoic acid (DHB). The relative amounts or concentrations of the peptide in each sample are determined by comparing the abundance (i.e., the mass spectrometric signal intensity and/or area) of the ions corresponding to the differentially isotopically-labeled peptides. When the volumes of the samples are not equal, the abundance determined for each peptide will have to be divided by the respective sample volume in order to determine the relative concentrations of the peptide in the samples.

The absolute quantitation of the amount or concentration of a peptide in a sample may be determined by using a known amount of an internal reference peptide. For example, a first sample containing an amount of a first peptide (or believed to contain an amount of a first peptide) could be provided along with a second sample containing a known or predetermined amount/concentration of a reference peptide. The first peptide and the reference peptide are the same peptide (i.e., have the same amino acid sequence) but are differentially isotopically-labeled. In some embodiments, the reference peptide could be chemically synthesized and could be differentially isotopically-labeled from peptides occurring in the first sample, thereby eliminating the need to isotopically label the peptide in the first sample. The reference peptide may also originate from other sources, such as, for example, biological protein-containing samples. After isolating the differentially isotopically-labeled first peptide and reference peptide, the peptides are analyzed by MALDI-MS to determine the relative amounts or concentrations of the first peptide in the sample and the reference peptide in the second sample. Because a predetermined amount/concentration of the reference peptide is used, the absolute amount and/or concentration of the peptide in the first sample may be calculated.

One or more of the samples containing the differentially isotopically-labeled peptides are typically derived from samples containing proteins. The proteins in such samples are digested to form peptides for analysis by MALDI-MS and/or MALDI-MS/MS. The proteins may be digested by any method, such as, for example, by chemical or enzymatic digestion. In a preferred embodiment, a digestion method is used that will not cleave a continuous epitope of the peptides to be analyzed. Reagents that may be used for chemical or enzymatic digestion of proteins include, but are not limited to trypsin, pepsin, protease Lys-C, protease Glu-C, protease V8, protease Arg-C, and cyanogen bromide (CNBr).

When one or more of the samples are derived from samples containing proteins, the present invention may be used to determine the relative (or absolute) amounts or concentrations of the protein in the protein-containing sample(s). The relative or absolute amounts or concentrations of the peptide will directly reflect the relative or absolute amounts or concentrations of the corresponding protein in the protein-containing sample, subject, of course, to any changes in volume or concentration between the protein-containing sample and the peptide-containing sample.

Isolating Peptides Using Antibodies for Discontinuous Epitopes

In order to isolate peptides using antibodies with paratopes for discontinuous epitopes of proteins or peptides, the protein or peptide must be isolated by the antibodies immobilized on a substrate before any digestion of the protein occurs under conditions such that the structure of the discontinuous epitope is not impaired (e.g., denatured), which might lead to loss of binding affinity or ability to bind to the antibody.

Once the protein is isolated by the antibodies on the substrate, the protein is subjected to digestion in order to produce a peptide or peptides bound to the antibodies. When a protein with a discontinuous epitope is subjected to digestion, one or more peptides may remain bound to the antibodies that may include only the amino acids of the discontinuous epitope or that may include the amino acids of the discontinuous epitope and other amino acids outside of the discontinuous epitope.

Isolated peptides that are isotopically-labeled may be achieved by isotopically labeling a protein or proteins before or after isolation of the protein by the antibodies immobilized on the substrate or by isotopically labeling the peptides resulting from digestion of a protein or proteins during or after digestion of the protein or proteins. Such methods are described in more detail below.

In some embodiments, a protein in a first sample and a protein in a second sample are differentially isotopically-labeled before the proteins are isolated. When such differentially isotopically-labeled proteins are digested, the peptides that result are differentially isotopically-labeled.

In other embodiments, a protein in a first sample may be isolated with one or more substrates with antibodies immobilized thereon and the protein in a second sample may be isolated with another substrate or substrates with antibodies immobilized thereon. The protein from the first sample and the protein from the second sample are thus isolated on different substrates such that the protein from the first sample and the protein from the second sample may be digested separately. This allows for differential isotopic labeling of the protein in the first sample and the protein in the second sample during or after digestion of the protein from the different samples that are isolated on different substrates. One or more of the substrates with peptides from the first sample and one or more of the substrates from the second sample are then positioned on a MALDI target together in order to analyze the peptides simultaneously using MALDI-MS and/or MALDI-MS/MS.

Discontinuous epitopes may be very large, thus necessitating the use of methods that extend the accessible m/z range of MALDI-MS or MALDI-MS/MS such as the use of higher laser power and/or using HCCA as the matrix. In addition, dual enzymatic digestion could be used to produce peptides from the discontinuous epitopes with lower molecular weights.

As discussed above, either before, during, or after isolating the differentially isotopically-labeled peptides on the substrate, the substrate is positioned on a MALDI target for analysis by MALDI-MS and/or MALDI-MS/MS. The differentially isotopically-labeled peptides are then analyzed by MALDI-MS to determine the relative abundances, which allows the determination of the relative and/or absolute amounts and/or concentrations of the peptide in the first sample and the second sample.

Samples

The peptides and proteins used in the present invention may originate from various sources. For example, the proteins and peptides may be chemically synthesized and/or may originate from biological samples such as body fluids (e.g., blood, urine, etc.), from cultured cells, from organ or tissue specimens, or from any other biological source or sources. The samples may contain a plurality of proteins and/or peptides or only a single protein or peptide.

Isotopic Labeling of Proteins/Peptides

Various methods of isotopic labeling are known in the art. Any method that results in peptides from different peptide- or protein-containing samples being differentially isotopically-labeled may be used. Although stable isotopes (e.g., $^1H$, $^2H$ (i.e., deuterium), $^{12}C$, $^{13}C$, $^{14}N$, $^{15}N$, $^{16}O$, $^{18}O$, etc.) are preferred, unstable isotopes may also be used. When the peptides are derived from proteins, the proteins in different samples may be differentially isotopically-labeled such that peptides resulting from digestion of the proteins will also be isotopically-labeled or the peptides may be differentially isotopically-labeled during or after digestion of the protein.

Examples of methods of providing differentially isotopically-labeled peptides include chemically modifying the peptides using chemicals having different isotopes incorporated therein (e.g., acetylation of peptides using acetic anhydride and hexadeutero acetic anhydride such that peptides from one sample include $CH_3CO$— and peptides from another sample include $CD_3CO$—), digesting protein-containing samples that were prepared using different isotope-enriched cell culture media (e.g., using isotopes of hydrogen (H), carbon (C), nitrogen (N), phosphorous (P), sulfur (S), etc.), and/or by labeling the peptides during digestion of the protein (e.g., enzymatically digesting different protein samples using $H_2{}^{16}O$ or $H_2{}^{18}O$ such that the peptides in different samples contain either $^{16}O$ or $^{18}O$ (e.g., as described in U.S. Patent Application Publication No. 2002/0076817)). Other methods of providing differentially isotopically-labeled peptides may be used, and a combination of methods may also be used.

It is preferable that the differential isotopic labeling of a protein or peptide does not interfere with the epitope recognition of a specific antibody. Analysis by mass spectrometric techniques described herein may be used to determine if such interference is occurring and, if interference is occurring, the peptides may be differentially isotopically-labeled by other techniques that do not interfere with the epitope recognition of the antibody.

Substrates with Immobilized Isolation Agents (e.g., Antibodies)

The methods of the present invention involve the use of one or more substrates with isolation agents (e.g., antibodies) immobilized thereon in order to isolate peptides and/or proteins. The isolation agents may be immobilized on a substrate directly or indirectly (e.g., using crosslinking agents), and such direct or indirect immobilization may be achieved through covalent or noncovalent bonding. The substrates may be made of various materials, may have various geometries, and may have varying sizes and volumes. Examples of suitable substrates include magnetic beads and agarose beads, although other materials (e.g., silicon, aluminum, glass, plastic, polycarbonate, polystyrene, polypropylene, polyethylene) and shapes of substrates could be used. It is preferred that the substrates used herein have a volume of 150 μm×150 μm×150 μm (i.e., 150 μm in length, 150 μm in height, and 150 μm in width) or less, more preferably $100^3$ μm$^3$ or less. It is also preferred that the substrates (in any shape) used herein have dimensions of 150 μm×150 μm×150 μm or less, more preferably 100 μm×100 μm×100 μm or less. In some preferred embodiments, the substrate or substrates are in the shape of beads having a diameter of 150 μm or less, more preferably having a diameter of 100 μm or less, even more preferably having a diameter of 30 μm-100 μm.

As stated above, each of the isolation agents on a substrate has an affinity or binding specificity for a peptide or protein. Although any isolation agent can be used, antibodies are preferred.

When antibodies are used as the isolation agent, each antibody has a binding specificity for an epitope (continuous or discontinuous) in the peptide and/or protein to be analyzed. Antibodies that have a binding specificity for a continuous epitope in the peptide and/or protein to be analyzed are preferred, as such continuous epitopes will be present even if a protein loses its tertiary structure. Antibodies with specificity for continuous epitopes without cleavage sites are even more preferable because the epitopes will be present after a protein is fragmented. Monoclonal antibodies that have a paratope for the continuous epitope in the peptide/protein are preferred because the paratopes of such monoclonal antibodies are uniform. However, polyclonal antibodies may also be used in the present invention. In addition, each substrate (e.g., agarose bead) preferably has only one type of antibody (i.e., antibodies with the same binding specificity) immobilized thereon, although multiple types of antibodies (i.e., antibodies with different binding specificities) could be immobilized on one substrate for use in the methods described herein.

Isolation agents (e.g., antibodies) and substrates may be commercially purchased and/or may be generated by known methods. For example, beads with or without antibodies immobilized thereon are commercially available from various vendors. In addition, methods of directly immobilizing and indirectly immobilizing (e.g., crosslinking) antibodies on substrates are known in the art. Furthermore, if antibodies needed for specific embodiments are not available, monoclonal and/or polyclonal antibodies may also be generated by methods known in the art.

Table I below lists commercially-available antibodies for cancer-related proteins that may be used in the present invention.

TABLE 1

| Antibody Name: | Company Name: | Cat #: | Source: |
|---|---|---|---|
| P53 (DO-1) | Santa Cruz | sc-126 | Mouse monoclonal |
| P21waf Ab-11 | Neo Markers | MS-891-p1 | Mouse monoclonal |
| P63 (4A4) | Santa Cruz | sc-8431 | Mouse monoclonal |
| PIG3 (AB-2) | Oncogene | OP148 | Mouse monoclonal |
| PUMA | Orbigen | pab-10277 | Rabbit polyclonal |
| TOPILA | TopoGen | 2010-1 | Mouse monoclonal |

Isolation of Peptides/Proteins by Isolation Agents (e.g., Antibodies) Immobilized on a Substrate The methods described herein involve isolating peptides and/or proteins in one or more samples using the isolation agents (e.g., antibodies) immobilized on a substrate. The isolation is typically carried out by incubating the immobilized isolation agents (e.g., antibodies) with the peptide- or protein-containing sample for a sufficient time and under appropriate conditions such that a desired or sufficient amount of the peptides/proteins are isolated for use in the methods described herein.

The peptides/proteins may be incubated by placing the sample or samples and the substrate or substrates together in an appropriate vessel or container. The substrates with immobilized isolation agents and isolated peptides/proteins are then placed on the MALDI target for analysis. Such an incubation method is useful for isolating peptides/proteins from samples having a small volume (e.g., 10 microliters (μl) or less), for isolating peptides/proteins from samples with a low concentration or amount (e.g., 10 femtomols (fmol) or less) of the peptide/protein to be isolated by the isolation agent (e.g., antibody), or for isolating peptides/proteins in embodiments where there is a low affinity (e.g., $K_D$ of $10^{-5}$ or less) between the isolation agent (e.g., antibody) and the peptide/protein to be isolated.

The peptides/proteins may also be incubated by placing the substrates with immobilized isolation agents on the MALDI target and then incubating the sample with the immobilized isolation agents directly on the MALDI target.

When peptides/proteins from two or more samples are to be isolated, the samples may be combined for incubation with the immobilized isolation agents (e.g., before or after placing the substrates on the MALDI target) or the samples may be incubated with the immobilized isolation agents separately (e.g., before or after placing the substrates on the MALDI target). In addition, any other incubation method or combination of methods may be used.

Determination of Peptide Sequence and Corresponding Protein

The present invention may also be used to determine the identity of the peptide and, for peptides originating from proteins, the identity of the protein from which the peptide originated (i.e., the corresponding protein) using MALDI-MS/MS. Generally, tandem mass spectrometry involves selecting a precursor ion in the first stage mass spectrometer, dissociating the component into fragments (e.g., by collision-induced dissociation (CID), which is accomplished by multiple collisions with an inert gas), and then analyzing the resulting fragments in the second stage mass spectrometer. Instruments capable of MALDI-MS/MS include, but are not limited to, the Applied Biosystems Div., Perkin-Elmer Corp. (Foster City, Calif.) API QSTAR™-Pulsar (QSTAR) and the Applied Biosystems (ABI) MALDI-TOF/TOF.

The amino acid sequence of the peptide in a sample may be determined by de novo sequencing or by database searching. Database searching allows identification of both the amino acid sequence and the protein corresponding to a peptide by searching one or more databases using data obtained from an MS/MS analysis (i.e., the MALDI-MS/MS spectrum). The fragment ions from the MALDI-MS/MS spectrum (along with the mass of the precursor ion and/or a MALDI-MS spectrum) are matched against a database of predicted fragment ions of various proteins and/or peptides. A score or rank is assigned for each the predicted fragment ions of the various proteins and/or peptides, which allows identification of the amino acid sequence of the peptide and the corresponding protein of which the peptide is a subsequence.

De novo sequencing also allows determination of the amino acid sequence of a peptide, and is accomplished by dissociating a selected peptide precursor ion such that the dominant resulting fragments are the result of cleavage at the amide bonds of the precursor peptide ion. The resulting ions include a series of ions with masses preferably differing by the mass of one amino acid residue, which allows the interpretation of the mass spectrum to determine the sequence of the peptide.

Amino acid sequence data determined by de novo sequencing may be used for database searching to look for one or more proteins with peptide sequences identical to, similar to, or homologous to the determined peptide sequence (i.e., one or more "corresponding proteins"). Such an approach is especially useful when a peptide originates from a protein that has not been sequenced (e.g., a protein from an organism whose genome/proteome has not been sequenced). Such database searching allows corresponding proteins identical to, similar to, and/or homologous to an unknown protein to be identified that contain the amino acid sequence of the peptide (or an amino acid sequence similar or homologous to the amino acid sequence of the peptide) as a subsequence.

Any database or combination of databases may be used to determine the identity of a peptide (i.e., the amino acid sequence of the peptide) and the identity of the protein corresponding to the peptide as well as to determine a protein containing an identical, similar, or homologous peptide corresponding to the amino acid sequence of a peptide determined by de novo sequencing. Examples of databases that may be used with the present invention include, but are not limited to, MASCOT (MatrixScience), Sonar (Proteometrics), Radars (Proteometrics), Profound (Rockefeller University), Prospector (University of California San Francisco), and FASTA. In addition, any algorithms and software programs useful in database searching and/or de novo sequencing may be used in the present invention such as, for example, the Basic Local Alignment Search Tool (BLAST) program (available at http://www.ncbi.nlm.nih.gov/BLAST).

Determination of Identity of Epitope-Containing Peptide or Identity of Epitope

In another aspect of the present invention, the identity of an epitope-containing peptide may be determined or the identity of a continuous or discontinuous epitope of peptide or protein may be determined. The epitope-containing peptides are isolated as discussed above using a substrate with immobilized isolation agents (e.g., antibodies). The identity of the epitope-containing peptide may then be determined by analyzing the peptide by MALDI-MS/MS and performing database searching and/or de novo sequencing.

In order to determine the exact epitope of a peptide or protein, enzymes may be used to digest all of the amino acids other than the epitope that is bound to a isolation agent such as an antibody. Then, by using MALDI-MS/MS, the identity of the epitope may be determined.

When the epitope or epitope-containing peptide originates from a protein, the peptide can be correlated to the identity of a corresponding protein by performing database searching using the results of the MALDI-MS/MS analysis. If necessary or desired, de novo sequencing may be performed to determine the amino acid sequence of the peptide, which may then be used to perform database searching for a corresponding protein.

ILLUSTRATIVE EMBODIMENTS

The methods are useful for various applications. For example, the methods described herein could be used to compare the level of a protein or proteins in a diseased state as compared to the level of the protein or proteins in a normal state, to compare the level of a protein or proteins in a diseased state to the level of protein or proteins in a different diseased state, to compare the level of a protein or proteins in samples after different treatments, to compare the level of a protein or proteins in samples from the same source before and after a treatment, or to compare the level of a protein or proteins in one stage of a disease to another stage of a disease.

In some embodiments, the methods of the present invention could be used to determine the expression level of multiple disease-related proteins concerning the same or different diseases. In such an embodiment, multiple antibodies specific to peptide epitopes from the multiple disease-related proteins would be immobilized on substrates preferably having only one type of antibody. The substrates could be placed, either before or after isolation of peptides by the antibodies, in a microarray format on a MALDI target plate for analysis by MALDI-MS and/or MALDI-MS/MS. In preferred embodiments, the formatting of the substrates could be such that each spot on a MALDI target will contain only one type of antibody. Such formatting and analysis could be automated.

In other embodiments, the methods of the present invention could be used (1) to compare the level of a protein or peptide in an unmodified state to the level of a protein or peptide in a modified state in the same or different samples or (2) to compare the level of a protein or peptide in a first modified state to the level of a protein or peptide in a second modified state in the same or different samples. For example, by using the methods described herein, the amount or concentration of an unphosphorylated peptide or protein could be relatively or absolutely quantified in one or more samples. The amount or concentration of the peptide or protein in a phosphorylated state could then be relatively or absolutely quantified in the same or different samples. The relative or absolute amounts or concentrations of the unphosphorylated peptide or protein in the one or more samples could then be compared to the relative or absolute amounts or concentrations of the phosphorylated peptide or protein in the sample or samples. A protein or peptide in any modification state (e.g., unmodified, modified, phosphorylated, unphosphorylated, etc.) could be compared to a protein or peptide in a different modification state. In some embodiments, the antibodies used to isolate the peptide or protein in one modification state could be different from the antibodies used to isolate the peptide or protein in a second modification state, and paratopes of such antibodies may include specificity for the modified portion or portions of the peptide or protein that are different between two different modification states.

Embodiment Shown in FIG. 1

FIG. 1 illustrates the analytical scheme of one embodiment of the invention for quantitative protein expression analysis using MALDI-MS. A sample containing the proteins of a proteome are digested to produce peptides, which are then acetylated using acetic anhydride (i.e., $(CH_3CO)_2O$) (step A) in order to incorporate $CH_3CO-$ into the peptides.

Standard/reference peptides of a known amount are added to the acetylated peptides in step B. The standard/reference peptides are acetylated using hexadeutero acetic anhydride (i.e., $(CD_3CO)_2O$) in order to incorporate $CD_3CO-$ such that the standard/reference peptides are differentially isotopically-labeled as compared to the peptides produced from the proteome digestion.

Antibodies that are immobilized on a substrate (e.g., a bead) are then added to the mixture (step C). Preferably, each substrate will contain only one type of antibody (i.e., all of the antibodies immobilized on a substrate will be have specificity for the same epitope). The immobilized antibodies are incubated with the peptide mixture in order to isolate the peptides that include the epitope for which the immobilized antibodies are specific.

After immunoprecipitation of the isotopically-labeled peptides, the immobilized antibodies are placed on a MALDI target plate in step D, one antibody substrate per spot in any order. The ordering of the particular antibody substrates is not important for identification purposes, as the identity of the peptides may be determined by MALDI-MS/MS. Inset D1 shows an enlargement of one spot on the MALDI target plate with one bead having immobilized antibodies with isolated peptides. Inset D2 shows an enlargement of a portion of the bead in inset D1 along with one antibody immobilized thereon and one peptide isolated by the antibody. As shown in inset D2, the peptide includes either $CD_3CO-$ or $CH_3CO-$.

A MALDI matrix solution is then added to the bound peptides (step E), which releases the peptides from the antibodies and allows MALDI-MS analysis of the peptides. Inset E1 shows that the MALDI matrix solution releases the peptides from the antibodies.

In step F, the peptides are analyzed by MALDI-MS to produce a mass spectrum for each of the spots on the MALDI target. The relative intensities of the ion signals corresponding to the $H_3$-labeled and the $D_3$-labeled peptide is used to quantify the amount of each specific peptide in the digestion sample relative to the standard/reference peptide. As stated above, the absolute amount of a specific peptide in the digestion sample can be determined by using the known amount of the standard/reference peptide added to the digestion sample. Finally, the relative and absolute quantitative amounts of a peptide can be used to determine the relative and absolute quantitative amounts of the protein from which the peptide originated, as the relative and absolute quantitative amounts of the peptide will correspond directly with the relative and absolute quantitative amounts of the protein in the original proteome sample.

It is noted that this embodiment may be performed using other labeling methods, may be used with or without a standard peptide, and may be performed using additional peptide samples.

Figure 2:
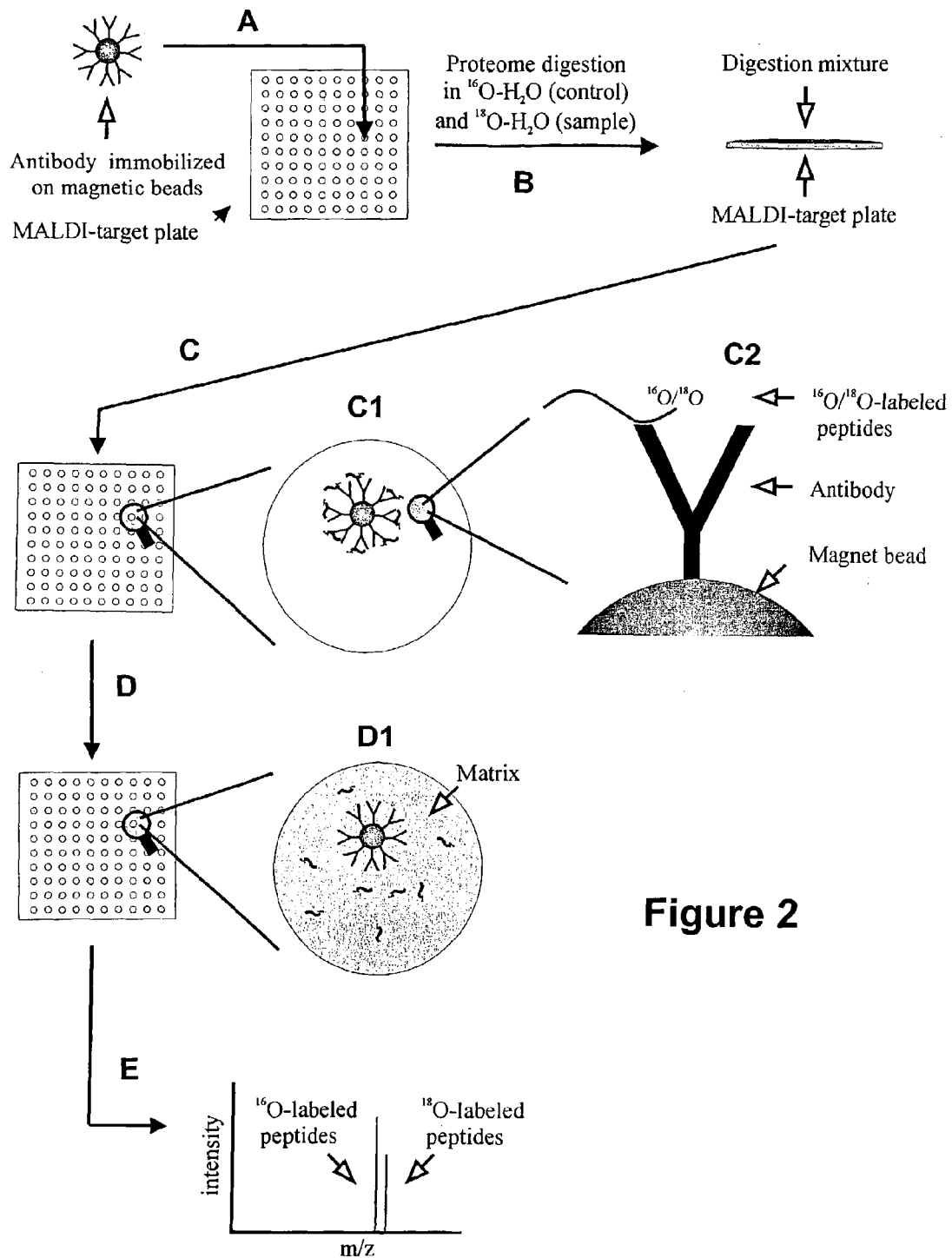
FIG. 2 illustrates an analytical scheme of another embodiment of a method for quantitative peptide/protein expression analysis using MALDI-MS.

Embodiment Shown in FIG. 2

FIG. 2 illustrates an embodiment of the invention in which the antibody beads are arranged on a MALDI target plate before the peptides are isolated by the antibodies. In step A, specific types of antibody are immobilized on magnetic beads and the beads are placed on a MALDI target plate in a microarray/spot format. As in the embodiment described in FIG. 1, each bead will contain only one type of antibody. However, multiple beads having antibodies of the same type may be placed in each MALDI spot if desired.

In step B, differentially isotopically-labeled peptides from two samples are added to the MALDI target plate. The differentially isotopically-labeled peptides are the product of digesting two protein-containing samples, one being digested in $^{16}O-H_2O$ and the other being digested in $^{18}O-H_2O$.

The differentially isotopically-labeled peptides are then incubated with the immobilized antibodies (step C). Inset C1 shows an enlargement of one spot on the MALDI target plate with one bead having immobilized antibodies with isolated peptides. Inset C2 shows an enlargement of a portion of the bead in inset C1 along with one antibody immobilized thereon and one peptide isolated by the antibody. As shown in inset C2, the peptide includes either $^{16}O$ or $^{18}O$.

A MALDI matrix solution is added to the spots in step D. Inset D1 shows that the MALDI matrix solution releases the peptides from the antibodies.

In step E, MALDI-MS is performed on one of the spots to produce the shown mass spectrum. The relative intensities of the ion signals corresponding to $^{16}O$-labeled and $^{18}O$-labeled peptides reflects the differential expression of the protein corresponding to the peptide in the original protein-containing samples.

It is noted that this embodiment may be performed using other labeling methods, may be used with or without a control peptide, and may be performed using additional peptide samples.

EXAMPLES

The invention will be further explained by the following illustrative examples that are intended to be non-limiting.

Example 1

Figure 3:
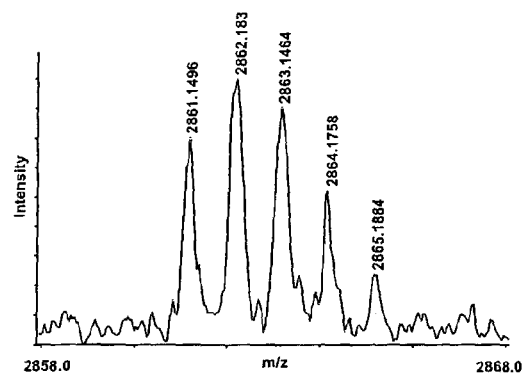
FIG. 3 illustrates a mass spectrum obtained by performing MALDI-MS on 12 femtomols of FLAG-tagged peptide affinity bound to a single antibody bead.

This example illustrates that MALDI-MS can be performed on peptides affinity-bound to a single antibody bead and that such mass spectrometry can be performed on low femtomole (fmol) amounts of affinity-bound peptide sample. A single antibody bead having 12 fmol of FLAG peptide (i.e., MDYKDHDGDYKDHDIDYKDDDK) affinity bound thereto was placed on a MALDI target and analyzed by MALDI-MS. FIG. 3 is the mass spectrum that was obtained by the MALDI-MS analysis. The theoretical peak of the protonated FLAG peptide is m/z 2861.15, but was seen at 2861.1496 as shown in FIG. 3 along with peaks at m/z 2862.183, 2863.1464, 2864.1758, and 2865.1884 of naturally-occurring isotopic variations of the peptide that were present. The spectrum demonstrates that high mass accuracy and resolution between the baseline-separated naturally-occurring isotopes of the is maintained even at low fmol amounts of peptide.

Example 2

This example confirms that the methods of the present invention are suitable for quantitation of peptides and proteins.

Two samples containing amounts of an AU-epitope peptide (i.e., DTYRYI) were differentially isotopically-labeled by acetylation with acetic anhydride and with hexadeutero acetic anhydride such that the resulting peptides were labeled with $H_3$ and $D_3$, respectively. The peptides were then isolated by anti-AU antibody beads and analyzed by MALDI-MS.

The experiment was performed twice. In one experiment, the amounts of the peptides in the samples were unknown. In the second experiment, the amounts of the peptides in the samples were also unknown, but three times as much of the $D_3$-labeled peptide-containing sample was used in the second experiment while the same amount of the $H_3$-labeled peptide-containing sample was used.

Figure 4A:
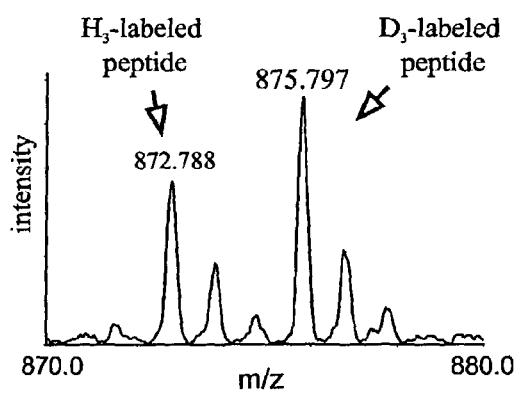
FIG. 4A and FIG. 4B each illustrate the mass spectrum of two differentially isotopically-labeled samples of an AU-epitope peptide. The peptides were differentially isotopically-labeled by acetylation with acetic anhydride and hexadeutero acetic anhydride such that the peptides were labeled with $H_3$ and $D_3$, respectively. Three times as much $D_3$-labeled peptide was used in FIG. 4B as in FIG. 4A.

FIG. 4A shows the mass spectrum obtained in the first experiment. The peak for the $H_3$-labeled peptide appeared at m/z 872.788 and was clearly distinguishable from the peak for the $D_3$-labeled peptide, which appeared at 875.797. The ratio of the ion signals of the $D_3/H_3$-labeled peptides in the experiment was 1.5.

Figure 4B:
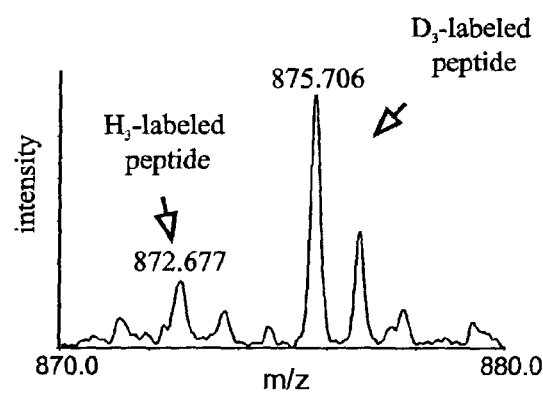

FIG. 4B shows the mass spectrum obtained in the second experiment. The peak for the $H_3$-labeled peptide appeared at m/z 872.677 and the peak for the $D_3$-labeled peptide appeared at m/z 875.706. The ratio of the ion signals of the $D_3/H_3$-labeled peptides in the experiment was 4.2.

As stated above, three times as much $D_3$-labeled peptide-containing sample was used in the second experiment as compared to the first experiment while the same amount of the $H_3$-labeled peptide-containing sample was used in both experiments. Therefore, a difference in the ion signal ratios of the $D_3/H_3$-labeled peptides between experiment 2 and experiment 1 was expected to be equal to a factor of 3. Dividing the ion signal ratio of 4.2 determined in the second experiment by the ion signal ratio of 1.5 determined in the first experiment showed a difference of 2.8 between the ion signal ratios determined in the two experiments, which is an error of less than 10% from the expected difference of 3.

Example 3

Model peptides bound to beads containing immobilized anti-phosphotyrosine antibodies, anti-c-myc antibodies, and immobilized avidin were analyzed in order to evaluate the method of direct MALDI-MS/MS sequencing of epitope-containing peptides bound to affinity beads with respect to sensitivity, mass accuracy, and protein identification via database searching and de novo sequencing.

I. Materials

The kinase domain of the insulin receptor peptide (KDIR) (Thr-Arg-Asp-Ile-Tyr-Glu-Thr-Asp-Tyr-Tyr-Arg-Lys), the phosphorylated kinase domain of the insulin receptor peptide #3 (pKDIR) (Thr-Arg-Asp-Ile-Tyr-Glu-Thr-Asp-Tyr-pTyr-Arg-Lys), and the biotinylated kinase domain of the insulin receptor peptide (biotinKDIR) (Biotin-Thr-Arg-Asp-Ile-Tyr-Glu-Thr-Asp-Tyr-Tyr-Arg-Lys) were purchased from AnaSpec (San Jose, Calif.). The c-myc peptide (Cys-Glu-Gln-Lys-Leu-Ile-Ser-Glu-Glu-Asp-Leu) was purchased from Covance (Berkeley, Calif.). All peptides were used without further purification. Stock solutions were prepared at a concentration of 1 µg/µL in HPLC-grade water, and serially diluted with HPLC-grade water.

Immobilized antiphosphotyrosine antibody, avidin agarose, and monoclonal anti-FLAG M2 affinity resin beads were purchased from Sigma Chemical Co., and anti-myc 9E10 affinity beads were purchased from Covance (Berkeley, Calif.).

II. Methods

A. Incubation of Standard Peptides with Affinity Beads

Affinity binding for the standard peptides was carried out in compact reaction columns (CRCs) (USB Corporation, Cleveland, Ohio). A typical column volume for a sample of standard used in this example was 10 µL. The beads were washed with 1.5 mL of 1× phosphate-buffered saline (PBS) prior to incubation. The peptides were then incubated with the beads for 2 hours in an Eppendorf Thermomixer at 400 rpm at 25° C. For each standard, a series of different loadings (~2 pmol to 700 pmol) was incubated with the beads. After incubation, the beads were washed with 1.5 mL of 1×PBS. The beads were never allowed to dry out.

Details of the TACE (tumor necrosis factor-alpha converting enzyme) digestion and isolation of FLAG-tagged peptides described below were performed as described in Sunnarborg et al., Tumor Necrosis factor-alpha converting enzyme (TACE) regulated epidermal growth factor receptor ligand availability, J. Bio. Chem. 2002, 12838-12845. Briefly, the medium concentrate solution was incubated with ~1 µg recombinant human TACE extracellular domain at 37° C. for 4 hours, and reactions were stopped by addition of EDTA to 10 mM final concentration. Products containing the FLAG epitope were immunoprecipitated by overnight incubation with anti-FLAG M2 affinity resin in 50 mM Tris pH 7.4, 150 mM NaCl. The beads were washed 5 times with 50 mM ammonium bicarbonate, and a 0.5 µL aliquot of the settled beads was spotted on the MALDI target.

B. Mass Spectrometry

MALDI/TOF-MS was performed on a Bruker Instruments Co. (Billerica, Mass.) Reflex III, with pulsed ion extraction. MALDI-MS and MALDI-MS/MS were performed on an Applied Biosystems Div., Perkin-Elmer Corp (Foster City, Calif.) API QSTAR™-Pulsar (QSTAR), with argon as the collision gas. The instrument is equipped with a nitrogen laser operating at 337 nm.

For experiments on the Reflex III, recrystallized alpha-cyano-4-hydroxycinnamic acid (HCCA) (Aldrich, Milwaukee, Wis.) was used as the matrix. The solvent for HCCA was 45:45:10 ethanol:water:formic acid, and was used as a saturated solution. A premixed matrix solution containing 2,5-dihydrobenzoic acid (DHB) (Agilent Technologies Inc., Palo Alto, Calif.) was used without further dilution for experiments on the QSTAR. A 0.5 μL aliquot of the settled beads was spotted on the target, followed by 0.5 μL matrix solution, and the solution was allowed to dry at room temperature.

C. Calculation of the Amount of Peptide on the MALDI Target

Determining the exact amount of affinity-bound peptide applied to the MALDI target was difficult. The bed volume of the affinity beads was 10 μl, and 1/20 of the bed volume was spotted on the MALDI target. However, the entire 0.5 μl volume was not composed solely of beads. Between 800-1000 beads were present in 10 μl of beads. However, often only 15-30 beads were present on the MALDI target. Therefore, dividing the amount of peptide incubated with the beads by 25 (800 beads incubated divided by 30 beads on target) provides a maximum amount on the MALDI target. Practically, the amount of peptide is most likely much less than what was calculated. This is due to variations in the amount of beads used for immunoprecipitation, as well as the number of beads applied to the MALDI target. For example, if 1000 beads were used for immunoprecipitation, and only 15 were applied to the MALDI target, only 1.5% of the original peptide solution is present for MS analysis.

D. Database Searching

For searching and interpreting MALDI-MS/MS spectra, Mascot software was used. Searches considered only the *Homo sapiens* genome, and a mass accuracy of 100 ppm in the precursor ion mass and 0.1 Da in the product ion masses was entered. When applicable, a fixed modification of "Biotin (N-term)" or a variable modification of "Phospho (S,T) and Phospho (Y)" was entered. The nomenclature of Roepstorff and Fohlman, Proposal for a common nomenclature for sequence ions in mass spectra of peptides, Biomed. Mass Spectrom. 1984, 11, 601, later modified by Biemann, Contributions of mass spectrometry to peptide and protein structure, Biomed. Environ. Mass Spectrom. 1988, 16, 99-111, was used to identify all product ions.

III. Results

A. Phosphotyrosine/Anti-Phosphotyrosine Binding

Figure 5A:
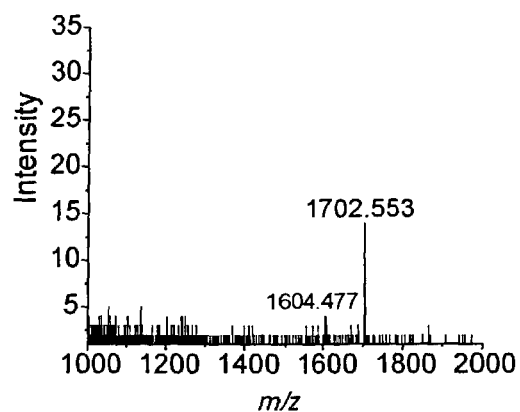
FIG. 5A shows the MALDI-MS spectrum of the pKDIR peptide affinity bound to immobilized anti-phosphotyrosine antibodies.
Figure 5B:
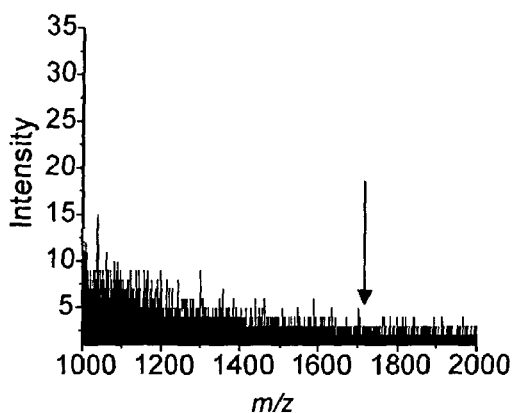
FIG. 5B shows the MALDI-MS spectrum of the pass through solution obtained from the incubation of the antibody beads with the pKDIR peptide used to produce the spectrum shown in FIG. 5A.

Phosphorylated pKDIR peptide at several concentrations was incubated with an antibody against phosphorylated tyrosine that was immobilized on agarose beads. FIG. 5A shows the MALDI-MS spectrum of the pKDIR peptide with a maximum of 234 fmol of affinity-bound peptide loaded on the target. The protonated molecule ([M+H]$^+$) at m/z 1702.553 of the phosphorylated peptide was observed, with a signal to noise ration (S/N) greater than 10, as well as a loss of 98 Da (m/z 1604.477), corresponding to loss of $H_3PO_4$, of approximately 25% relative intensity. The resolution obtained for the peak at m/z 1702.553 was 11,601. The ability of the antibody to completely capture all phosphorylated peptides was examined by performing MALDI-MS of the pass-through. As shown in FIG. 5B, no ion signal is observed at m/z 1702.5, indicating that the antibody beads selectively bound all peptide present in the solution.

Figure 5C:
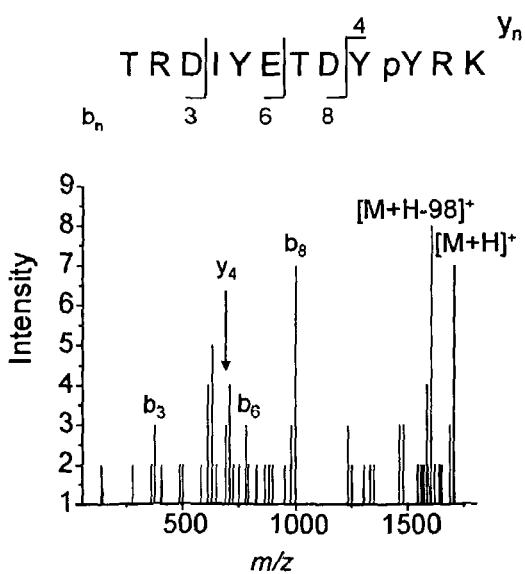
FIG. 5C illustrates the MALDI-MS/MS spectrum of the ion at m/z 1702.553 shown in FIG. 5A. The Figure also shows the amino acid sequence of the peptide corresponding to the ion at m/z 1702.553 as determined by database searching.

The MALDI-MS/MS spectrum of the ion at m/z 1702.553 is shown in FIG. 5C depicting several b and y ions. The six most abundant product ions from the MALDI-MS/MS spectrum were submitted to Mascot for database searching. Because this peptide does not correspond to an enzymatic fragment, no enzyme was specified in the search. Even without any enzyme restriction, the insulin receptor protein, along with several homologous proteins, was identified as the top hit, with an average error of 106 ppm in the product ions masses. (It is noted that this mass accuracy could be achieved even from ion signals with S/N=3.) Several proteins were identified as the top hit because each protein sequence contains the KDIR peptide. This demonstrates that analyzing peptides affinity-bound to antibody beads does not compromise the mass accuracy of the QqTOF. The ability to search MS/MS spectra, with high mass accuracy, is important for the unambiguous identification of peptides and especially for the identification of phosphorylation sites.

Figure 6A:
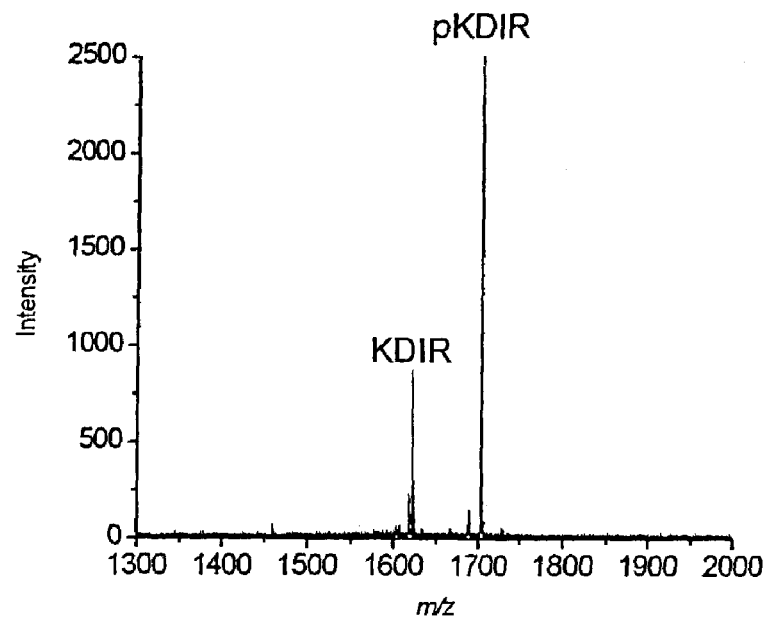
FIG. 6A illustrates the MALDI-MS spectrum of a mixture of KDIR peptide in its phosphorylated and unphosphorylated forms.
Figure 6B:
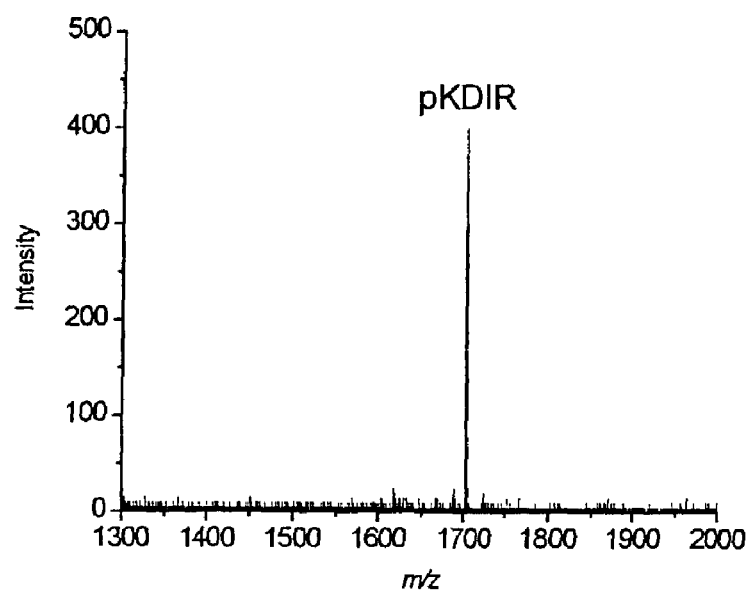
FIG. 6B illustrates the MALDI-MS spectrum obtained from analyzing immobilized anti-phosphotyrosine antibodies incubated with the mixture analyzed in FIG. 6A.

In order to test the specificity of the antibody, a mixture of the same KDIR peptide, in both its phosphorylated and its unphosphorylated form, was incubated with another aliquot of the antibody beads. A MALDI-MS spectrum of the mixture is shown in FIG. 6A. For accurate comparison, the same amount of peptide as that shown in FIG. 5A was applied to the beads. A MALDI-MS analysis of the beads after incubation, shown in FIG. 6B, illustrates that none of the unphosphorylated sequence was captured by the antibody, indicating that it is highly specific for phosphorylated tyrosine residues. This demonstrates that antiphosphotyrosine beads can be used to both isolate and concentrate phosphorylated peptide(s) of interest from a complex mixture.

B. Myc/Anti-myc Binding

Figure 7A:
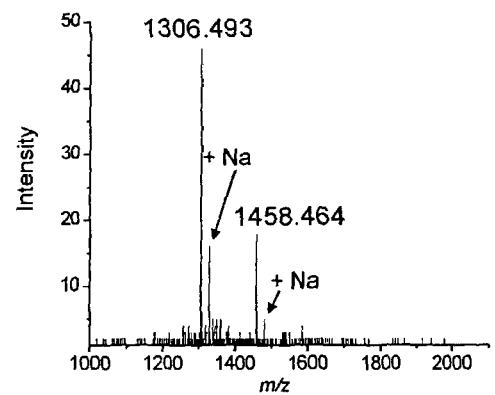
FIG. 7A illustrates the MALDI-MS spectrum obtained from incubating a standard peptide containing the c-myc epitope with agarose beads containing immobilized antibodies against the c-myc epitope.

Several concentrations of a standard peptide containing the c-myc epitope, from the human c-myc gene, were incubated with agarose beads containing an immobilized antibody against the c-myc epitope (EQKLISEEDL). A representative MALDI-MS spectrum of the peptide is shown in FIG. 7A. Although the solution incubated with the affinity beads was supposed to contain only a single peptide sequence, it was apparent from the MALDI-MS spectrum that two peptides containing the c-myc epitope were present at m/z 1306.493 and m/z 1458.464. A MALDI-MS spectrum of the control anti-c-myc antibody beads (i.e., beads without any sample being incubated) confirmed that there was no contamination from the beads at m/z 1458.464 (data not shown).

Figure 7B:
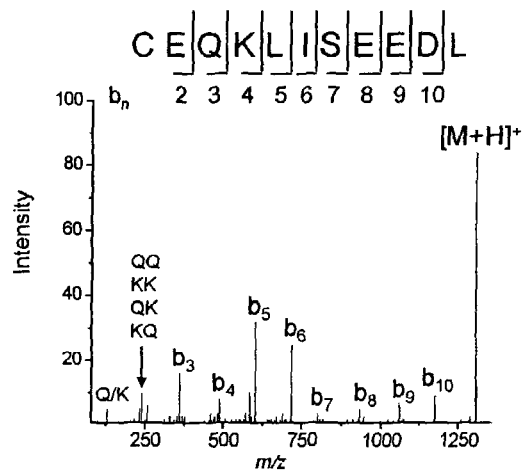
FIG. 7B illustrates the MALDI-MS/MS spectrum of the ion at m/z 1306.493 shown in FIG. 7A. The Figure also shows the amino acid sequence of the peptide corresponding to the ion at m/z 1306.493 as determined by database searching.
Figure 7C:
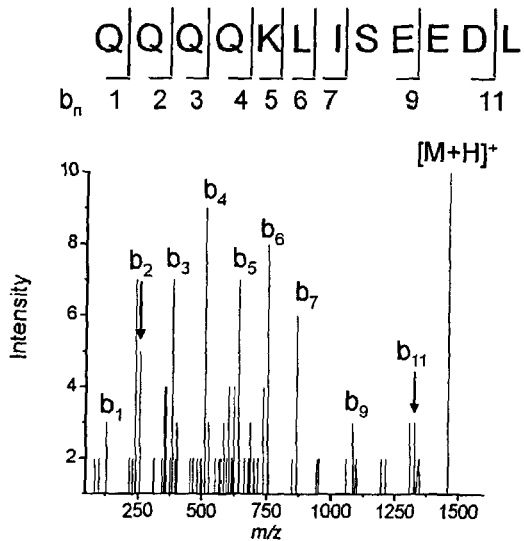
FIG. 7C illustrates the MALDI-MS/MS spectrum of the ion at m/z 1458.464 shown in FIG. 7A. The Figure also shows the amino acid sequence of the peptide corresponding to the ion at m/z 1458.464 as determined by de novo sequencing.

MALDI-MS/MS spectra of the peptides affinity-bound to the antibody beads are shown in FIGS. 7B and 7C. FIG. 7B is the MALDI-MS/MS spectrum of the ion at m/z 1306.493 and FIG. 7C is the MALDI-MS/MS spectrum of the ion at m/z 1458.464. To determine the complete peptide sequence, a slightly higher loading (a maximum of 3.1 pmol) was applied to the sample target in order to increase the number of sequence specific ions that would be observed. A complete b ion series, from $b_2$ to $b_{10}$, was observed for the expected sequence (CEQKLISEEDL) for the ion at m/z 1306.493. Because this peptide is a synthetic construct, and not present in a protein sequence, this MALDI-MS/MS spectrum was not submitted for database searching. The human myc proto-oncogene protein (Accession # P01106) has a Glu residue ($Glu^{416}$) preceding the epitope tag, instead of a Cys. FASTA (http://www.ebi.ac.uk/fasta33/) was used to search for homologous proteins, and the c-myc proto-oncogene protein was unambiguously identified. The average mass error observed in these experiments was ±85 ppm.

For the unexpected peptide detected at m/z 1458.464 in the synthetic standard, de novo sequencing was necessary to identify the amino acid sequence of the peptide. A series of ions, differing in mass by 128 Da was observed, which identified the first 4 residues of this peptide as Gln, and the fifth residue as Lys. With the high mass accuracy of the QqTOF, Lys (128.094 Da) and Gln (128.059 Da) can be differentiated, even though there is only a 0.04 Da difference. The remaining residues were identical in sequence to the expected peptide. A complete b ion series, from $b_1$ to $b_7$ was observed, as well as the $b_9$ and $b_{11}$ ions. Due to the $b_8$ and $b_{10}$ ions not being observed, amino acid pairs were determined from the mass differences measured between the $b_7$ and $b_9$ ions, as well as the $b_9$ and $b_{11}$ ions.

This c-myc experiment emphasizes the importance of being able to rapidly perform MS/MS sequencing of affinity-bound peptides. Although the c-myc epitope has been reported to be (EQKLISEEDL), the peptide at m/z 1458.464 only has a portion of this epitope tag (QKLISEEDL), yet was still immunoprecipitated by the anti-c-myc antibody. Partial epitope recognition can lead to cross-reactivity and isolation of contaminating proteins. The methods described herein were able to quickly identify all proteins isolated by the antibody.

C. Biotin/Avidin Binding

Figure 8A:
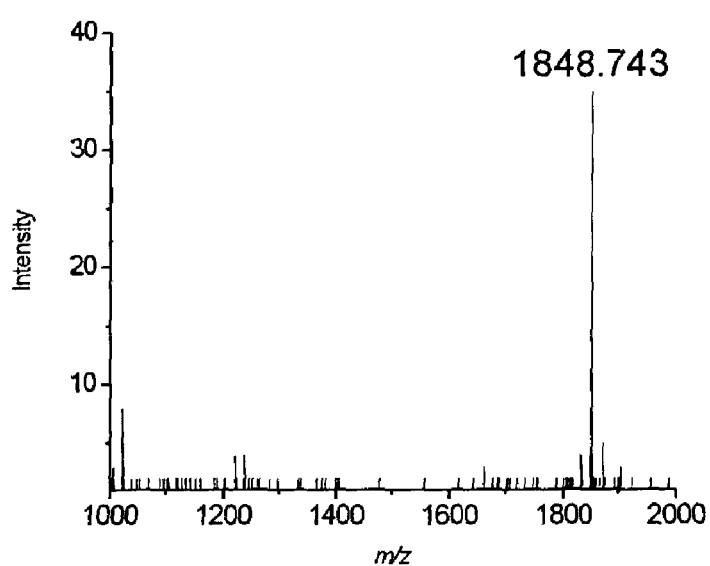
FIG. 8A illustrates the MALDI-MS spectrum obtained from incubating biotinKDIR peptide with agarose beads containing immobilized avidin moiety.
Figure 8A:
Figure 8B:
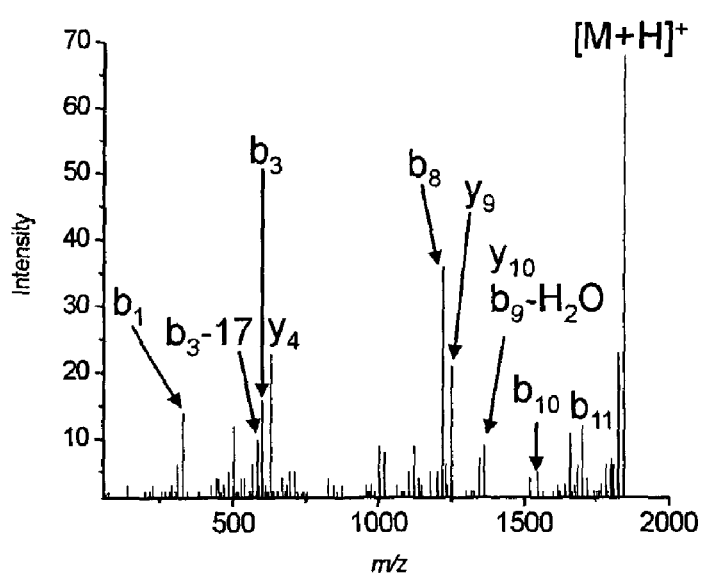
FIG. 8B illustrates the MALDI-MS/MS spectrum of the ion at m/z 1848.743 shown in FIG. 8A. The Figure also shows the amino acid sequence of the peptide corresponding to the ion at m/z 1848.743 as determined by database searching.

The biotinKDIR peptide was incubated with agarose beads containing an immobilized avidin moiety. Because the biotin avidin association is one of the strongest noncovalent interactions, initially an aliquot of beads containing a maximum of 2.16 pmol of affinity-bound peptide was placed on the MALDI target and analyzed. The MALDI-MS spectrum of the peptide is shown in FIG. 8A. Strong signal is observed for the protonated molecule ($[M+H]^+$), with a S/N ratio greater than 30. MALDI-MS/MS was performed on the ion at m/z 1848.743, and the MALDI-MS/MS spectrum is shown in FIG. 8B. Several sequence specific b and y ions were observed, which were sufficient for identifying the peptide sequence.

Figure 9:
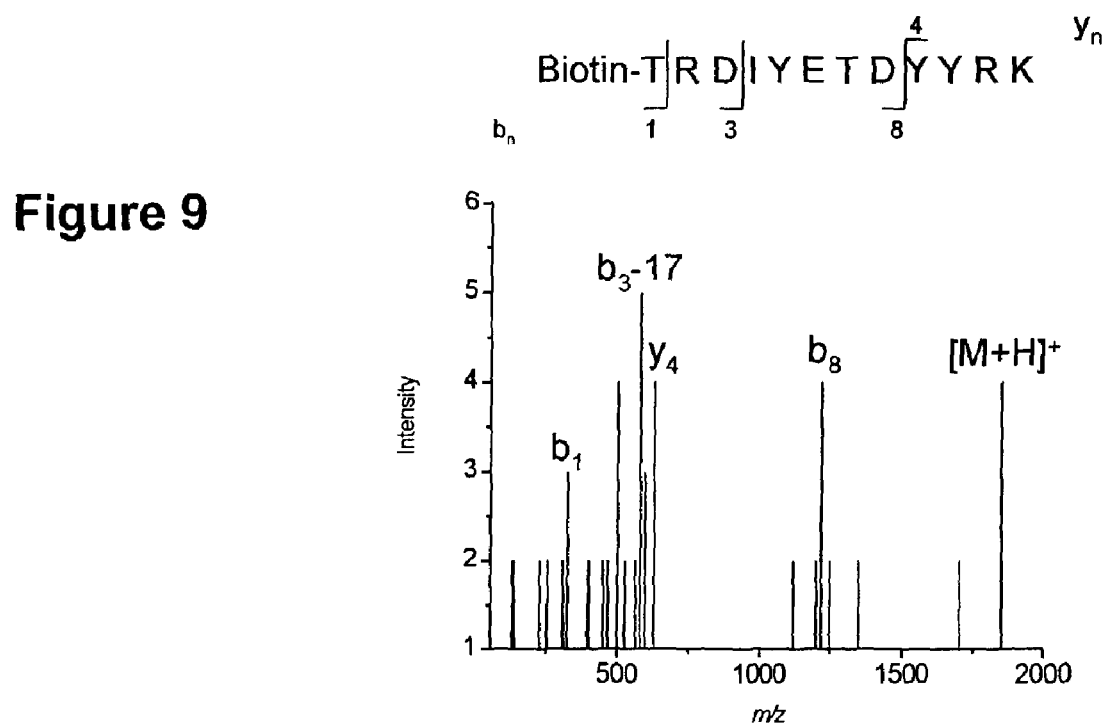
FIG. 9 illustrates the MALDI-MS/MS spectrum obtained from incubating biotinKDIR peptide with agarose beads containing immobilized avidin moiety of the ion at m/z 1848.743 using less sample than was used in FIGS. 8A and 8B. The Figure also shows the amino acid sequence of the peptide corresponding to the ion at m/z 1848.743 as determined by database searching.

A lower sample loading (<250 fmol loading) was used on the MALDI plate to obtain the MALDI-MS/MS spectra shown in FIG. 9. This MALDI-MS/MS spectrum was obtained with a maximum of 216 fmol spotted on the target. Although only four product ions are present with a S/N greater than 2, the mass accuracy was high enough to identify the protein by database searching, specifying a fixed modification of N-terminal biotinylation. The insulin receptor (Accession# NP_000199), along with several variants, was identified, with an average error of 65 ppm in the product ion masses. Even with mid-femtomole amounts of sample applied to the MALDI target, the protein can unambiguously be identified via database searching.

Although the biotin-avidin association ($K_d=10^{-15}$M) is stronger than the biotin-streptavidin association ($K_d=10^{-13}$M), the standard biotinylated peptide was easily dissociated from the avidin agarose under MALDI conditions. Thus, even compounds with high dissociation constants can still be measured using direct MALDI-MS/MS of peptides affinity-bound to antibody beads.

Figure 10A:
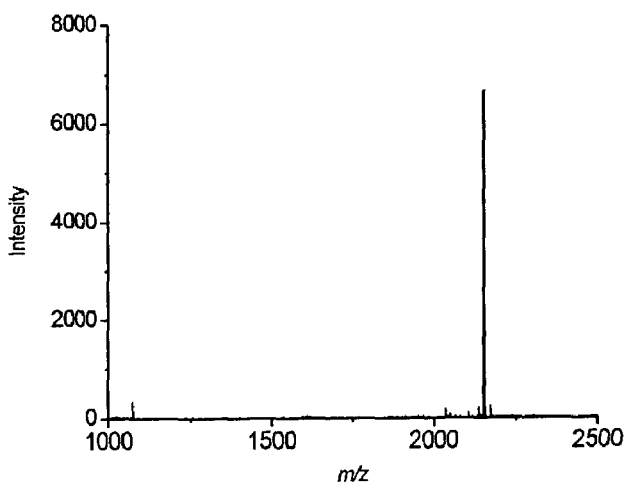
FIG. 10A illustrates a MALDI-MS spectrum obtained by incubating a standard FLAG-tagged peptide with beads containing immobilized anti-FLAG antibody and then irradiating the beads with the laser.
Figure 10B:
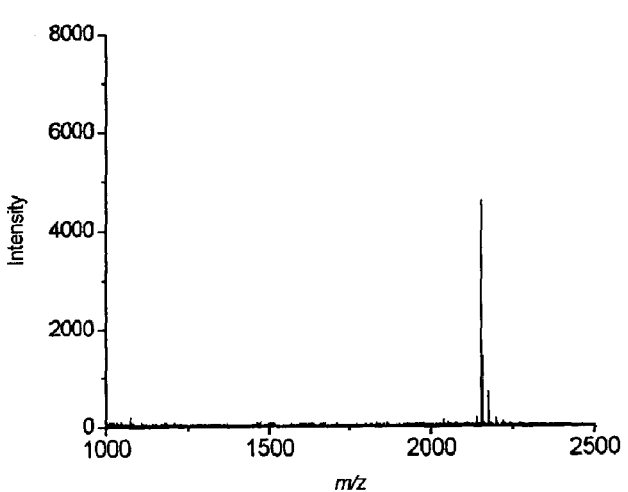
FIG. 10B illustrates a MALDI-MS spectrum obtained by incubating a standard FLAG-tagged peptide with beads containing immobilized anti-FLAG antibody and then irradiating the matrix crystals (and not the beads) with the laser.

D. Determination of Whether or not the Peptides are Bound to the Antibody Beads Following the Addition of Matrix Solution To test whether or not peptides are released from antibody beads during the spotting process, a standard peptide bound to beads containing an immobilized anti-FLAG antibody, was spotted with HCCA. MALDI-MS spectra were acquired when beads were irradiated by the laser (FIG. 10A) and when only matrix crystals were irradiated by the laser (FIG. 10B). It is clear that some elution occurs, as strong signal is obtained when the laser irradiates only matrix crystals. However, there is greater signal intensity when the beads are in the laser path, indicating that some peptide may remain bound to, or closely-associated with, the antibody beads during the spotting process.

Figure 10C:
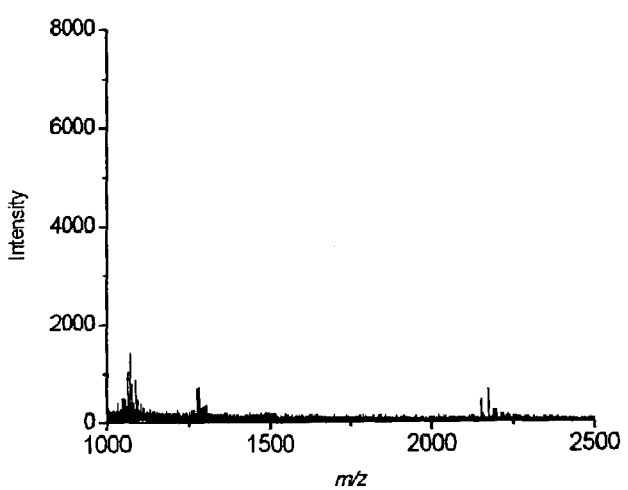
FIG. 10C illustrates a MALDI-MS spectrum obtained by incubating a standard FLAG-tagged peptide with beads containing immobilized anti-FLAG antibody and then irradiating matrix crystals formed from HCCA and methanol (and without formic acid) with the laser.

To determine whether the acid or the organic solvent was responsible for the release of the peptide from the antibody beads, an aliquot of the beads was spotted using only HCCA and methanol as the matrix solution. The MALDI-MS spectrum acquired with no beads in the laser path (FIG. 10C) indicates that very little peptide was released from the beads. Therefore, it appears that the addition of acid to the matrix solvent that promotes peptide release from the antibody beads. Regardless of whether the peptides remain bound or are eluted, spotting the affinity beads directly on the MALDI target allows detection of femtomole amounts of peptide with the ability to perform MS and MS/MS analysis.

E. Application of the Method to Identify In Vitro Proteolysis Products of TACE

MALDI-MS and MALDI-MS/MS were used to assess the ability of tumor necrosis factor alpha converting enzyme (TACE) to cleave a membrane-proximal site in pro-transforming growth factor $\alpha$ (proTGF$\alpha$).

TGF$\alpha$ is a member of the epidermal growth factor (EGF) family. TGF$\alpha$ is generated as a membrane bound precursor (proTGF$\alpha$) that is proteolytically cleaved to release the EGF receptor binding ligand. Until recently, the identities of the enzymes required for proteolytic processing were unknown. A novel protease, tumor necrosis factor-$\alpha$ converting enzyme (TACE), was identified as being responsible for converting the membrane-bound pro-TGF$\alpha$ to its soluble form (see Sunnarborg et al., Tumor Necrosis factor-alpha converting enzyme (TACE) regulated epidermal growth factor receptor ligand availability, J. Bio. Chem. 2002, 12838-12845). A soluble epitope-tagged version of the ectodomain of proTGF$\alpha$ (proTGFecto) was created with a C-terminal FLAG tag (DYKDDDDKVV). Media concentrate solution from cells expressing this construct was incubated with recombinant human TACE extracellular domain for 4 hours at 37° C. Anti-FLAG M2 affinity resin was subsequently added at the end of the incubation. Immunoprecipitates were washed with 50 mM ammonium bicarbonate and a small aliquot of the beads was directly placed on the MALDI target.

Figure 11A:
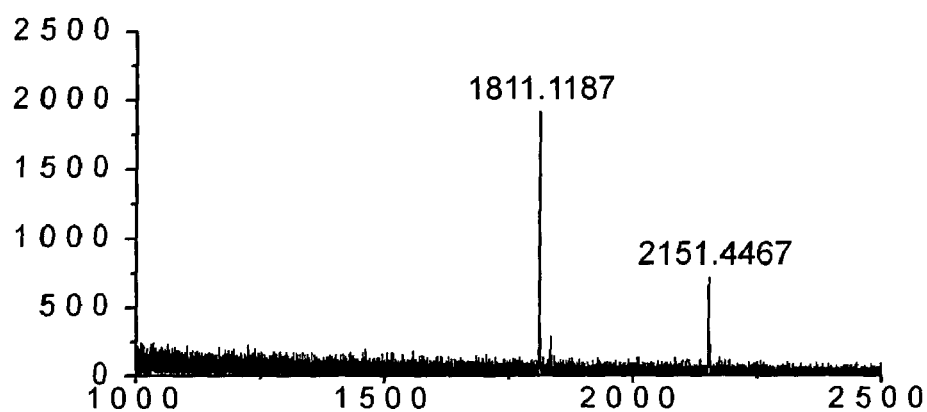
FIG. 11A illustrates the MALDI-MS spectrum obtained after incubating a soluble FLAG-tagged version of the ectodomain of proTGFα (proTGFecto) with recombinant human TACE extracellular domain and then adding beads with anti-FLAG affinity resin.

Two peaks were observed in the MALDI-TOF/MS spectrum at m/z 2151.447 and 1811.119, as shown in FIG. 11A. The peak at 2151.447 matched the molecular weight of a synthetic peptide with the sequence of the expected product, VVAASQKKQDYKDDDDKVV with cleavage occurring between Ala[89] and Val[90] (m/z 2151.350). Because the second product (at m/z 1811.119) was unexpected, its sequence was determined by MALDI-MS/MS.

Figure 11B:
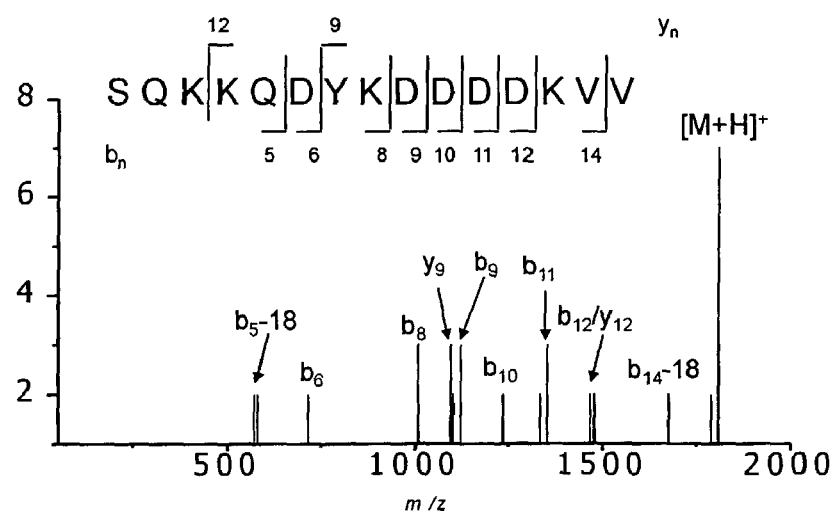
FIG. 11B illustrates the MALDI-MS/MS spectrum of the ion at m/z 1811.119 shown in FIG. 11A. The Figure also shows the amino acid sequence of the peptide corresponding to the ion at m/z 1811.119 as determined by database searching.

The MALDI-MS/MS product ion spectrum of the ion at m/z 1811.119 is shown in FIG. 11B. Although the overall intensity was low, a series of b ions identified the sequence of the peptide as SQKKQDYKDDDDKVV, thus confirming a second in vitro TACE cleavage site on proTGFecto, between Ala[94] and Ser[95]. Determination of the sequence of the ion at m/z 1811.119 therefore allowed unambiguous confirmation of the identity of an unexpected proteolytic product, thereby providing an indication of a second, specific cleavage event.

IV. Conclusions

This example illustrates a powerful method for isolation, identification, and sequencing of peptides bound to immobilized antibodies on affinity beads. Placing an aliquot of the affinity beads directly on the MALDI target eliminates sample loss that can occur with peptide elution followed by nanoelectrospray ionization tandem mass spectrometry (nESI-MS/MS), which is the usual method of choice for peptide sequencing. Direct on-target analysis of affinity-bound analytes is also a much more rapid approach than the previously used MALDI-based technique involving enzymatic ladder sequencing of affinity-bound peptides.

The high mass accuracy of the QqTOF mass spectrometer is not affected by the direct MALDI analysis of affinity-bound peptide beads. With this high mass accuracy, commercially-available proteomics software packages such as Mascot can identify a protein from the MS/MS spectrum of one of its peptides, and can automatically localize the modification to a specific amino acid within that peptide, even when the peptide is affinity-tagged. Thus, the method is well suited for molecular characterization of epitope-containing peptides.

Example 4

Figure 12:
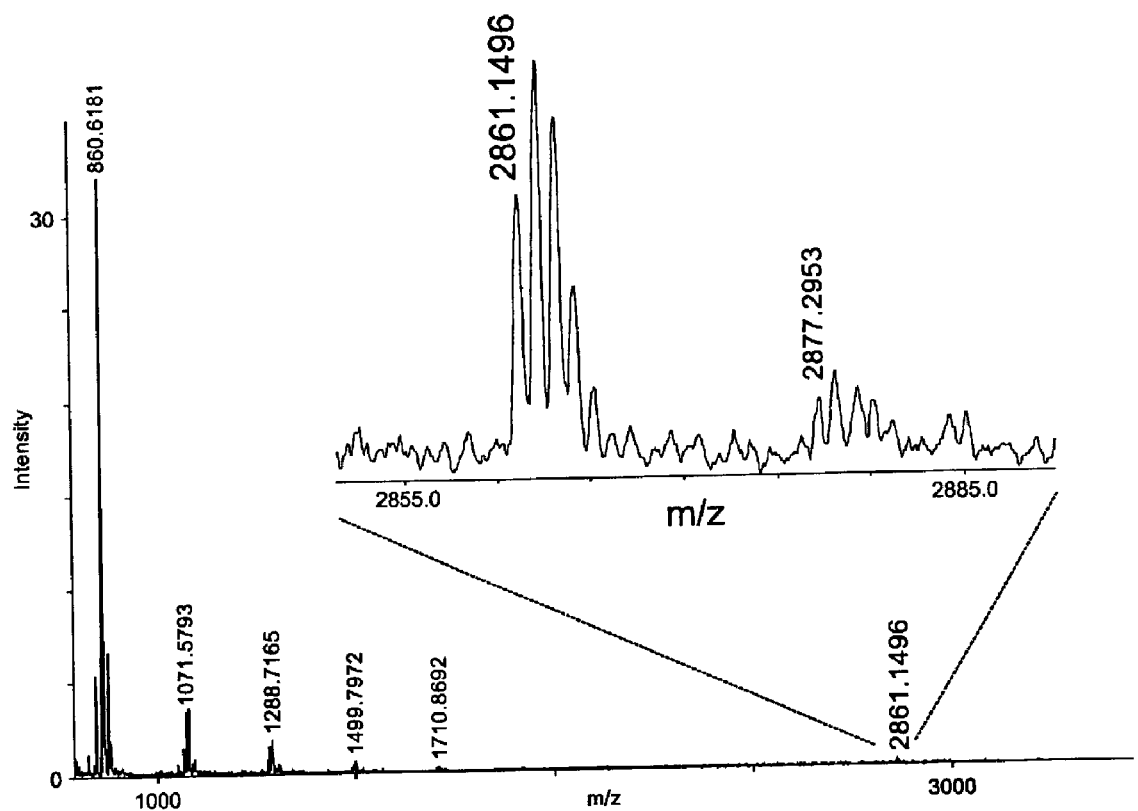
FIG. 12 illustrates a mass spectrum obtained by performing MALDI-MS on 12 femtomols of FLAG-tagged peptide affinity bound to a single antibody bead.

FIG. 12 illustrates the MALDI-MS spectrum of 12 fmol of FLAG peptide (i.e., MDYKDHDGDYKDHDIDYKDDDK) affinity bound to a single antibody bead obtained according to the present invention. The theoretical peak of the protonated [M+H]$^+$ FLAG peptide is m/z 2861.15, but was seen at 2861.1496 as shown in FIG. 12. The ion signal at m/z 2877.2953 corresponds to oxidized FLAG peptide that was present. Based on the intensity of the ion signals, the oxidized FLAG peptide is present in an amount approximately 10% to that of the FLAG peptide at m/z 2877.2953, which demonstrates that the methods described herein may detect peptides present at approximately 1 femtomol.

Example 5

Varying ratios of amounts of differentially isotopically-labeled AU-peptide (i.e., DTYRYI) were isolated on antibody beads and then analyzed using MALDI-MS according to the present invention to determine the ratios of the differentially isotopically-labeled AU-peptide. The AU-peptide was differentially isotopically-labeled using acetic anhydride and hexadeutero acetic anhydride such that the labeled peptides included $CH_3CO$— and $CD_3CO$—, respectively. The following ratios of $CH_3CO$-labeled peptide (referred to as "H" in this example) to $CD_3CO$-labeled peptides (referred to as "D" in this example) were used: 1:10, 1:3, 1:1 (two data points collected), 3:1, and 10:1. The theoretical and determined $CH_3CO$—(H):$CD_3CO$-(D) ratios are shown below in Table 2.

TABLE 2

| Theoretical H:D ratio | Determined H:D ratio |
| --- | --- |
| 1 | 0.9745 |
| 10 | 7 |
| 3 | 2.313 |
| 1 | 0.82 |
| 0.33 | 0.36 |
| 0.1 | 0.0778 |

Figure 13:
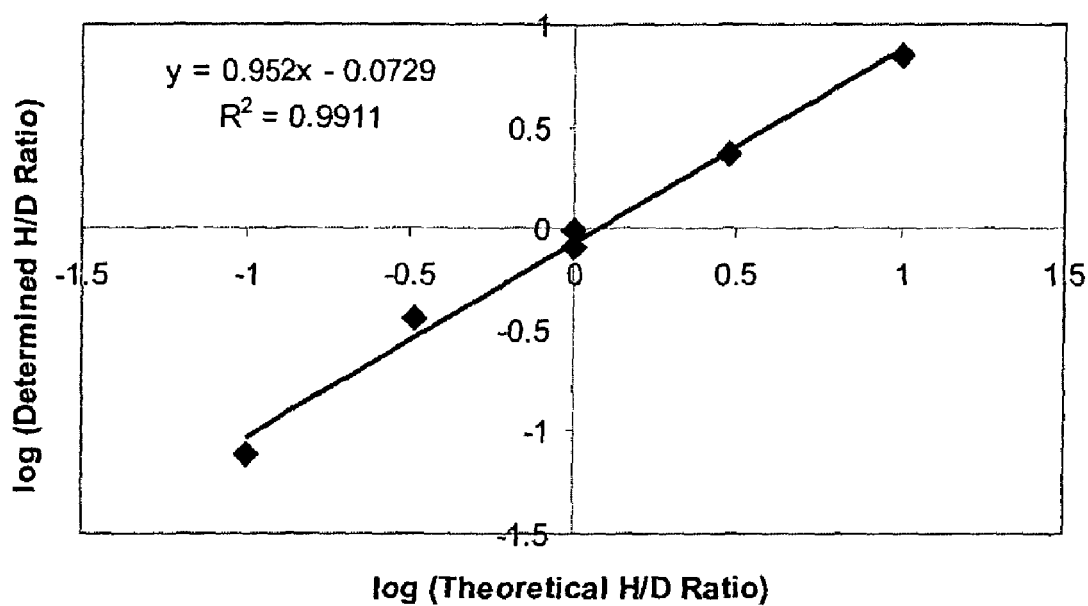
FIG. 13 illustrates a plot of the log of the theoretical ratios of $CH_3CO$-/$CD_3CO$-labeled peptides against the log of the calculated ratios of the $CH_3CO$-/$CD_3CO$-labeled peptides as determined by a method according to the present invention.

The log of the theoretical H:D ratios was plotted against the log of the determined H:D ratios as shown in FIG. 13. The figure illustrates linearity across two orders of magnitude.

Example 6

Figure 14:
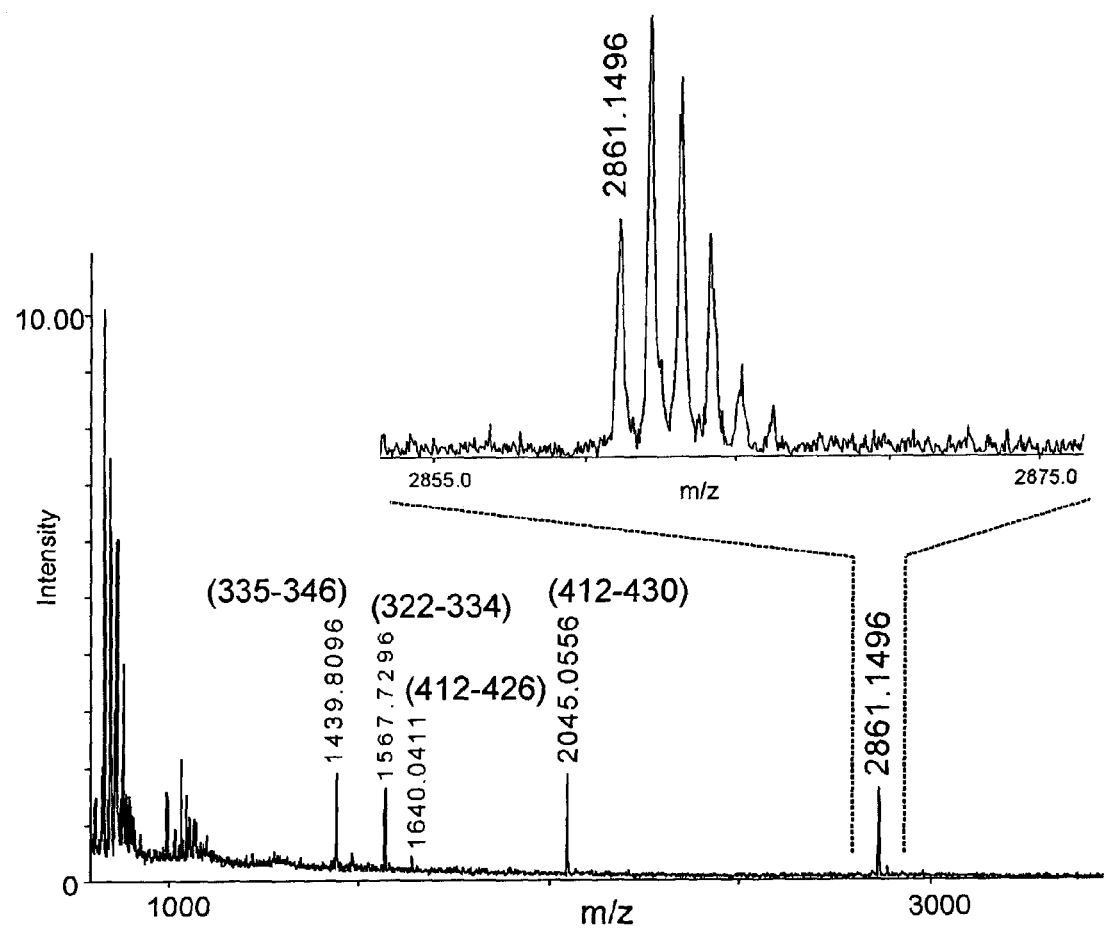
FIG. 14 illustrates a mass spectrum obtained by performing MALDI-MS on 12 femtomols of FLAG peptide affinity bound to a single antibody bead. The 12 femtomols of FLAG peptide was isolated by incubating the affinity bead with a mixture of 1.2 picomols of FLAG peptide and 180 picomols of a BSA digestion mixture.

In order to demonstrate the feasibility of using the methods of the present invention with peptides present at low concentrations in a complex mixture, approximately 1.2 pmol of FLAG peptide ([M+H]$^+$=2861.15) was mixed with approximately 180 pmol of a digestion mixture of bovine serum albumin (BSA). One hundred (100) beads with immobilized anti-FLAG antibodies were incubated with the FLAG peptide/BSA digestion mixture and then one of the beads (containing approximately 12 fmol of FLAG peptide) was placed on a MALDI target. After addition of matrix, MALDI-MS was performed to obtain the MALDI-MS spectrum shown in FIG. 14. The spectrum shows ion signals corresponding to the FLAG peptide at m/z 2861.15 (along with naturally-occurring isotopic variations thereof) along with four tryptic peptides from the BSA digestion mixture at m/z 1439.80, 1567.73, 1640.04, and 2045.06. The amino acid sequence of the tryptic peptides from BSA is shown above the m/z value of the ion signals.

While the invention has been described in detail and with reference to specific embodiments thereof, it will be apparent to one skilled in the art that various changes and modifications can be made without departing from the spirit and scope of the invention.

What is claimed is:

1. A method of quantifying the amount or concentration of a peptide in two different samples, the method comprising the steps of:

(a) providing a first sample containing an amount of a peptide and a second sample containing an amount of the peptide, the peptide in the first sample and the peptide in the second sample being differentially isotopically-labeled such that the peptide in the first sample has a different molecular weight than the peptide in the second sample, the peptide having a continuous epitope, wherein the peptide comprises 2 to 22 amino acids;

(b) providing a bead having a volume and having a plurality of antibodies immobilized thereon, each of the antibodies having a paratope specific to the continuous epitope of the peptide;

(c) positioning the isotopically-labeled peptides for analysis by matrix-assisted laser desorption/ionization mass spectrometry (MALDI-MS), comprising:

i) isolating the differentially isotopically-labeled peptides using the antibodies immobilized on the bead by exposing the first and second samples to the antibodies; and ii) placing the bead having the antibodies immobilized thereon on a MALDI target, wherein the bead having the antibodies immobilized thereon is placed on a MALDI target before, during, or after the differentially isotopically-labeled peptides are isolated using the antibodies on the bead; and (d) analyzing the differentially isotopically-labeled peptides using MALDI-MS to determine the relative amounts or concentrations of the peptide in the first sample and the second sample.

2. The method of claim 1 wherein the amount of the first peptide in the first sample is known and wherein, after the relative amounts or concentrations of the first and second peptides are determined, the absolute amount or concentration of the second peptide is determined based on the known amount of the first peptide in the first sample.

3. The method of claim 1 wherein the first sample is provided by digesting a first protein-containing sample such that the first peptide originates from a first protein and wherein the second sample is provided by digesting a second protein-containing sample such that the second peptide originates from a second protein.

4. The method of claim 3 wherein the method further comprises determining the relative amounts or concentrations of the first and second proteins in the first and second protein-containing samples.

5. The method of claim 3 wherein the peptides are differentially isotopically-labeled before, during, or after the first and second protein-containing samples are digested.

6. The method of claim 1 wherein at least one of the first sample or the second sample is provided by digesting a protein-containing sample such that at least one of the first or second peptides originates from a protein.

7. The method of claim 1 further comprising identifying the amino acid sequence of one or both of the differentially isotopically-labeled peptides.

8. The method of claim 7 wherein the amino acid sequence of one or both of the differentially isotopically-labeled peptides is determined by analyzing one or both of the differentially isotopically-labeled peptides using matrix-assisted laser desorption/ionization tandem mass spectrometry (MALDI-MS/MS) and performing de novo sequencing using the results of the MALDI-MS/MS analysis.

9. The method of claim 7 wherein the amino acid sequence of one or both of the differentially isotopically-labeled peptides is determined by analyzing one or both of the differentially isotopically-labeled peptides using matrix-assisted laser desorption/ionization tandem mass spectrometry (MALDI-MS/MS) and performing database searching using the results of the MALDI-MS/MS analysis.

10. The method of claim 6 wherein the method further comprises correlating at least one of the first or second peptides with the identity of the protein from which it originated.

11. The method of claim 10 wherein the correlating comprises determining the amino acid sequence of at least one of the first or second peptides and searching a database for at least one protein sequence that contains the amino acid sequence as a subsequence of the protein.

12. The method of claim 10 wherein the correlating comprises analyzing one or both of the differentially isotopically-labeled peptides using matrix-assisted laser desorption/ionization tandem mass spectrometry (MALDI-MS/MS) and performing database searching using the results of the MALDI-MS/MS analysis.

13. The method of claim 1 wherein the peptides are differentially isotopically-labeled using stable isotopes.

14. The method of claim 1 wherein the bead has a volume ranging from 30 µm×30 µm×30 µm to 150 µm×150 µm×150 µm.

15. The method of claim 1 wherein the bead provided in step (b) has no other antibodies immobilized thereon.

16. The method of claim 3, wherein at least one peptide in the first sample and the peptide in the second sample are differentially isotopically labeled during or after the first and second protein-containing samples are digested.

17. A method of quantifying the amount or concentration of a peptide in two different samples, the method comprising the steps of:
  (a) providing a first sample containing an amount of a peptide and a second sample containing an amount of the peptide, the peptide in the first sample and the peptide in the second sample being differentially isotopically-labeled such that the peptide in the first sample has a different molecular weight than the peptide in the second sample, the peptide having a continuous epitope, wherein the peptide comprises 2 to 22 amino acids;
  (b) providing a bead having a volume ranging from 30 µm×30 µm×30 µm to 150 µm×150 µm×150 µm and having a plurality of antibodies immobilized thereon, each of the antibodies having a paratope specific to the continuous epitope of the peptide;
  (c) positioning the isotopically-labeled peptides for analysis by matrix-assisted laser desorption/ionization mass spectrometry (MALDI-MS), comprising:
    iii) isolating the differentially isotopically-labeled peptides using the antibodies immobilized on the bead by exposing the first and second samples to the antibodies; and
    iv) placing the bead having the antibodies immobilized thereon on a MALDI target, wherein the bead having the antibodies immobilized thereon is placed on a MALDI target before, during, or after the differentially isotopically-labeled peptides are isolated using the antibodies on the bead; and
  (d) analyzing the differentially isotopically-labeled peptides using MALDI-MS to determine the relative amounts or concentrations of the peptide in the first sample and the second sample.

* * * * *

SEQUENCE LISTING

```
<160> NUMBER OF SEQ ID NOS: 12

<210> SEQ ID NO 1
<211> LENGTH: 22
<212> TYPE: PRT
<213> ORGANISM: Artificial Sequence
<220> FEATURE:
<223> OTHER INFORMATION: FLAG peptide

<400> SEQUENCE: 1

Met Asp Tyr Lys Asp His Asp Gly Asp Tyr Lys Asp His Asp Ile Asp
 1               5                  10                  15

Tyr Lys Asp Asp Lys
            20

<210> SEQ ID NO 2
<211> LENGTH: 6
<212> TYPE: PRT
<213> ORGANISM: Artificial Sequence
<220> FEATURE:
<223> OTHER INFORMATION: AU-epitope peptide

<400> SEQUENCE: 2
```

```
Asp Thr Tyr Arg Tyr Ile
1               5

<210> SEQ ID NO 3
<211> LENGTH: 4
<212> TYPE: PRT
<213> ORGANISM: Artificial Sequence
<220> FEATURE:
<223> OTHER INFORMATION: insulin receptor peptide

<400> SEQUENCE: 3

Lys Asp Ile Arg
1

<210> SEQ ID NO 4
<211> LENGTH: 12
<212> TYPE: PRT
<213> ORGANISM: Artificial Sequence
<220> FEATURE:
<223> OTHER INFORMATION: insulin receptor peptide

<400> SEQUENCE: 4

Thr Arg Asp Ile Tyr Glu Thr Asp Tyr Tyr Arg Lys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: c-myc peptide

<400> SEQUENCE: 5

Cys Glu Gln Lys Leu Ile Ser Glu Glu Asp Leu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: c-myc epitope

<400> SEQUENCE: 6

Glu Gln Lys Leu Ile Ser Glu Glu Asp Leu
1               5                   10

<210> SEQ ID NO 7
<211> LENGTH: 9
<212> TYPE: PRT
<213> ORGANISM: Artificial Sequence
<220> FEATURE:
<223> OTHER INFORMATION: epitope tag

<400> SEQUENCE: 7

Gln Lys Leu Ile Ser Glu Glu Asp Leu
1               5

<210> SEQ ID NO 8
<211> LENGTH: 10
<212> TYPE: PRT
<213> ORGANISM: Artificial Sequence
<220> FEATURE:
<223> OTHER INFORMATION: C-terminal FLAG tag

<400> SEQUENCE: 8
```

-continued

```
Asp Tyr Lys Asp Asp Asp Lys Val Val
 1               5                10

<210> SEQ ID NO 9
<211> LENGTH: 19
<212> TYPE: PRT
<213> ORGANISM: Artificial Sequence
<220> FEATURE:
<223> OTHER INFORMATION: synthetic peptide

<400> SEQUENCE: 9

Val Val Ala Ala Ser Gln Lys Lys Gln Asp Tyr Lys Asp Asp Asp
 1               5                   10                  15

Lys Val Val

<210> SEQ ID NO 10
<211> LENGTH: 15
<212> TYPE: PRT
<213> ORGANISM: Artificial Sequence
<220> FEATURE:
<223> OTHER INFORMATION: b ions peptide

<400> SEQUENCE: 10

Ser Gln Lys Lys Gln Asp Tyr Lys Asp Asp Asp Lys Val Val
 1               5                   10                  15

<210> SEQ ID NO 11
<211> LENGTH: 12
<212> TYPE: PRT
<213> ORGANISM: Artificial Sequence
<220> FEATURE:
<223> OTHER INFORMATION: m/z 1848.743 peptide

<400> SEQUENCE: 11

Thr Arg Asp Ile Tyr Glu Thr Asp Tyr Tyr Arg Lys
 1               5                   10

<210> SEQ ID NO 12
<211> LENGTH: 12
<212> TYPE: PRT
<213> ORGANISM: Artificial Sequence
<220> FEATURE:
<223> OTHER INFORMATION: m/z 1458.464 peptide

<400> SEQUENCE: 12

Gln Gln Gln Gln Lys Leu Ile Ser Glu Glu Asp Leu
 1               5                   10
```